United States Patent [19]

Boyd et al.

[11] Patent Number: 5,591,770
[45] Date of Patent: Jan. 7, 1997

[54] CALANOLIDE AND RELATED ANTIRETROVIRAL COMPOUNDS, COMPOSITIONS, AND USES THEREOF

[75] Inventors: Michael R. Boyd, Ijamsville; John H. Cardellina, II, Walkersville; Kirk R. Gustafson, Mt. Airy; James B. McMahon, Frederick; Richard W. Fuller, Tracy's Landing; Gordon M. Cragg, Bethesda, all of Md.; Yoel Kashman, Tel Aviv, Israel; Doel Soejarto, Lombard, Ill.

[73] Assignees: The United States of America as represented by the Department of Health and Human Services, Washington, D.C.; The Board of Trustees of the University of Illinois, Urbana, Ill.

[21] Appl. No.: 65,618

[22] Filed: May 21, 1993

Related U.S. Application Data

[63] Continuation-in-part of Ser. No. 861,249, Mar. 31, 1992.
[51] Int. Cl.⁶ .................... A61K 31/365; A61K 31/37; C07D 493/22
[52] U.S. Cl. ................... 514/453; 514/457; 514/460; 549/277
[58] Field of Search ................... 549/277; 514/460, 514/457, 453; 424/88

[56] References Cited

FOREIGN PATENT DOCUMENTS

WO92/06695  4/1992  WIPO .................. A61K 31/74

OTHER PUBLICATIONS

Saunders, "Non–nucleoside inhibitors of HIV reverse transcriptase"..., Drug Design & Discovery 8:255–263 (1993).
Ranjith et al., *Phytochemistry*, 24 (7), 1553–1556 (1985).
Bandara et al., "Two Chemically Distinct Groups of *Calophyllum* species From Sri Lanka," *Phytochemistry*, 25(2), 425–428 (1986).
Boyd, "Strategies for the Identification of New Agents for the Treatment of AIDS: A National Program to Facilitate the Discovery and Preclinical Development of New Drug Candidates for Clinical Evaluation," (Chapter 18) In *AIDS: Etiology, Diagnosis, Treatment and Prevention*, 2d edition, (DeVita, Jr. et al., eds., J. B. Lippincott Co., Philadelphia, 1988).
Boyer et al., "Analysis of Nonnucleoside Drug–Resistant Variants of Human Immunodeficiency Virus Type 1 Reverse Transcriptase," *J. Virology*, 67(4), 2412–2420 (1993).
Cragg et al., "Conservation of Biodiversity and the Potential for Development of Pharmaceutical Crops: Drug Discovery and Development at the United States National Cancer Institute," In *Proceedings of the Symposium on The Industrial Utilization of Tropical Plants and the Conservation of Biodiversity*, Enugu, Nigeria, Feb. 14–19, 1993 (in press).
Craig et al., "Antiviral properties of Ro 31–8959, An Inhibitor of Human Immunodeficiency Virus (HIV) Proteinase," *Antiviral Research*, 16, 295–305 (1991).
Dahanayake et al., "Chemical Investigation of Ceylonese Plants. Part VII. Extractives of *Calophyllum thwaitesii* Planch and Triana and *Calophyllum walkeri* Wight (Guttiferae)," *J. C. S. Perkin I* 2510–2514 (1974).

(List continued on next page.)

*Primary Examiner*—Michael P. Woodward
*Attorney, Agent, or Firm*—Leydig, Voit, & Mayer, Ltd.

[57] ABSTRACT

The present invention provides novel antiviral compounds, refered to as calanolides, related compounds, and their derivatives, which may be isolated from plants, or derived from compounds from plants, of the genus Calophyllum in accordance with the present inventive method. The compounds and their derivatives may be used alone or in combination with other antiviral agents in compositions, such as pharmaceutical compositions, to inhibit the growth or replication of a virus, such as a retrovirus, in particular a human immunodeficiency virus, specifically HIV-1 or HIV-2.

24 Claims, 10 Drawing Sheets

OTHER PUBLICATIONS

Dharmaratne et al., "Triterpenoids and Coumarins from the Leaves of *Calophyllum Cordato–Oblongum,*" *Phytochemistry,* 24(7), 1553–1556 (1985).

Dharmaratne et al., "Xanthones from Roots of Three *Calophyllum Series*", *Phytochemistry,* 25(8), 1957–1959 (1986).

Gautier et al., "Structure of Calophynic Acid, A Novel Constituent of *Calophyllum Inophyllum,*" *Tetrahedron Letters,* 27, 2715–2718 (1972).

Gulakowski et al, "A Semiautomated Multiparameter Approach for Anti–HIV Drug Screening," *Journal of Virological Methods,* 33, 87–100 (1991).

Gunasekera et al., "Chemical Investigation of Ceylonese Plants. Part 27. Extractives of *Calophyllum cuneifolium* Thw. and *Calophyllum soulattri* Burm. f. (Guttiferae)," *J. C. S. Perkin I,* 1505–1511 (1977).

Gunasekera et al., "Chemical Investigation of Ceylonese Plants. Part XVI. Extractives of *Calophyllum cordato–oblongum* Thw. (Guttiferae)," *J.C.S. Perkin I,* 2215–2220 (1975).

Gunatilaka et al., "Terpenoid and Biflavonoid Constituents of *Calophyllum Calaba* and *Garcinia Spicata* From Sri Lanka," *Phytochemistry,* 23(1), 323–328 (1984).

Gustafson et al., "A Nonpromoting Phorbol from the Samoan Medicinal Plant *Homalanthus nutans* Inhibits Cell Killing by HIV–1," *J. Med. Chem.,* 35, 1978–1986 (1992).

Gustafson, et al., "AIDS–Antiviral Natural Products Research at the U.S. National Cancer Institute," in *Natural Products as Antiviral Agents* (Chu et al., eds., Plenum Press, New York 1992).

Hertzberg et al., "Kenetic Studies of HIV–1 Reverse Transcriptase Inhibition by Inophyllums, A Novel Class of Non–Nucleoside Inhibitors, Using a Scintillation Proximity Assay," *Program and Abstracts of the Third International Conference on the Biotechnology of Microbial Products: Novel Pharmacological and Agrobiological Activities,* P–42, 27 (Apr. 1993).

Hertzberg et al., "Novel Methods for Antiviral Drug Discovery," *Programs and Abstracts of the Third International Conference on the Biotechnology of Microbial Products: Novel Pharmacological and Agrobiological Activities,* S–9, 17 (Apr. 1993).

Hizi et al., "Specific Inhibition of the Reverse Transcriptase of Human Immunodeficiency Virus Type 1 and the Chimeric Enzymes of Human Immunodeficiency Viruses Type 1 and Type 2 by Nonnucleoside Inhibitors," *Antimicrob. Agents Chemother.,* 37, 1037–1042 (1993).

Kashman et al., "The Calanolides, a Novel HIV–Inhibitory Class of Courmarin Derivatives from the Tropical Rainforest Tree, *Calophyllum lanigerum,*" *J. Med. Chem.,* 35, 2735–2743 (1992).

Kumar et al., "Calocalabaxanthone, The Putative Isoprenyl Precursor of Calabaxanthone From *Calophyllum Calaba,*" *Phytochemistry,* 21(3), 807–809 (1982).

Mabberlay, *The Plant Book,* (p. 92) (Cambridge University Press, 1987).

McCaffrey et al., "A Rapid Fluorometric DNA Assay for the Measurement of Cell Density and Proliferation In Vitro," *In Vitro Cellular & Developmental Biology,* 24(3, Part I), 247–252 (Mar., 1988).

Merigan, "Treatment of AIDS with Combinations of Antiretroviral Agents," *Amer. J. of Medicine,* 90(suppl. 4A), 8S–17S (Apr. 10, 1991).

Ohtani et al., "Absolute Configuration of Marine Diterpenes Possessing a Xenicane Skelton. An Application of an Advanced Mosher's Method," *Tetrahedron Letters,* 30(24), 3147–3150 (1989).

Ohtani et al., "A New Aspect of the High–Field NMR Application of Mosher's Method. The Absolute Configuration of Marine Triterpene Sipholenol–A," *J. Org. Chem.,* 56, 1296–1298 (1991).

Patil et al., "The Inophyllums, Novel Inhibitors of HIV–1 Reverse Transcriptase," *Programs and Abstracts of the Third International Conference on the Biotechnology of Microbial Products: Novel Pharmacological and Agrobiological Activities,* P–31, 26 (Apr. 1993).

Pauwels et al., "Potent and selective inhibition HIV–1 Replication In Vitro by A Novel Series of TIBO Derivatives," *Nature,* 343, 470–474 (1990).

Rink et al., "Cytoplasmic pH and Free $Mg^{2+}$ in Lymphocytes," *J. of Cell Biology,* 95, 189–196 (Oct., 1982).

Samaraweera et al., "Calozeylanic Acid, A New Bark Acid From Three *Calophyllum Species,*" *Tetrahedron Letters,* 22(50), 5083–5086 (1981).

Shih et al., "Chimeric Human Immunodeficiency Virus Type 1/Type 2 Reverse Transcriptases Display Reversed Sensitivity to Nonnucleoside Analog Inhibitors," *Proc. Natl. Acad. Sci. USA,* 88, 9878–9882 (Nov. 1991).

Soejarto et al., "Challenges in Developing a New Drug from Tropical Rain Forest Plants," In *Proceedings of the Symposium on the Industrial Utilization of Tropical Plants and the Conservation of Biodiversity,* Enugu, Nigeria, Feb. 14–19, 1993 (in press).

Somanathan et al., "Chemical Investigation of Ceylonese Plants. Part VIII. Trapezifolixanthone, a New Di–isoprenylated Xanthone from the Bark of *Calophyllum trapezifolium* Thw. (Guttiferae)," *J. C. S. Perkin I, 2515–2517 (1974).*

Stout et al., "*Calophyllum* Products III. The Structures of Blancoic Acids," *J. of Organic Chemistry,* 33, 4185–4190 (1968).

Stout et al., "The Structure of Costatolide," *J. of Organic Chemistry,* 29, 3604–3609 (1964).

Swagler et al., "Pharmacokinetics of Anti–HIV Nucleosides in Microswine," *J. Pharm. Pharmacol.,* 43, 823–826 (1991).

Vydac Reverse Phase HPLC Brochure, 26–27 (1992).

Weislow et al., "New Soluble–Formazan Assay for HIV–1 Cytopathic Effects: Application to High–Flux Screening of Synthetic and Natural Products for AIDS–Antiviral Activity," *J. National Cancer Institute,* 81(8), 577–586 (Apr. 19, 1989).

White et al., "A TIBO Derivative, R82913, Is A Potent Inhibitor of HIV–1 Reverse Transcriptase with Heteropolymer Templates," *Antiviral Research,* 16, 257–266 (1991).

Chaturvedi, et al., "Anticonvulsant and Antiinflammatory Activity of Natural Plant Coumarins and Triterpenoids", *Research Communications In Chemical Pathology and Pharmacology,* 9(1), 11–22 (Sep. 1974).

Kawazu et al., "Piscicidal Constituents of Capophyllum Inophyllum", *Chemical Abstracts,* 78(3), 207 (Jan. 22, 1973).

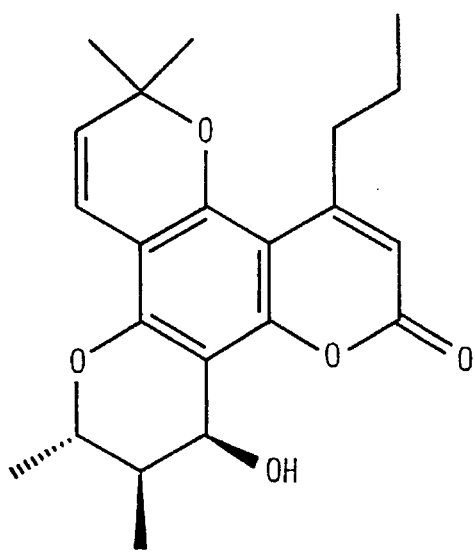
9
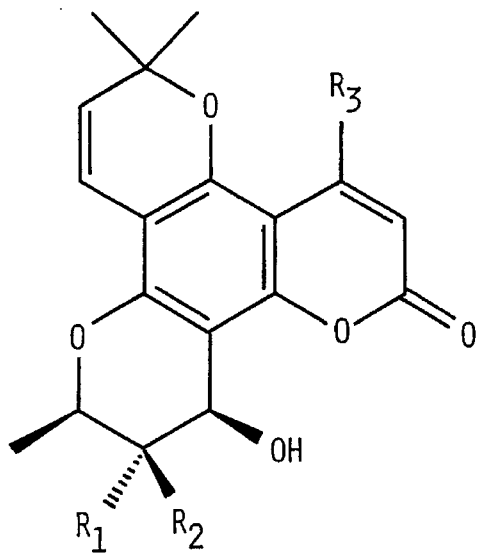
10 $R_1 = CH_3, R_2 = H, R_3 = C_6H_5$
11 $R_1 = CH_3, R_2 = H, R_3 = CH_3$
12 $R_1 = H, R_2 = CH_3, R_3 = C_6H_5$
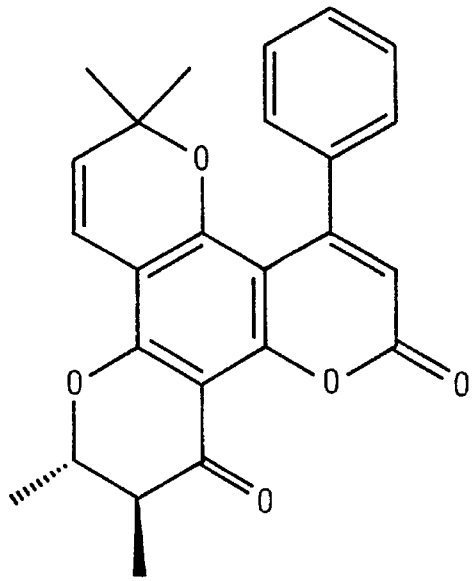
13
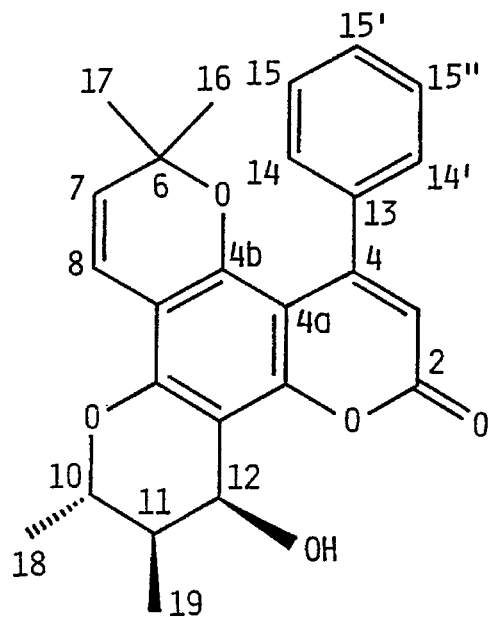
14
FIG. 2

Calanolide A- MTPA ester

Calanolide B - MTPA ester

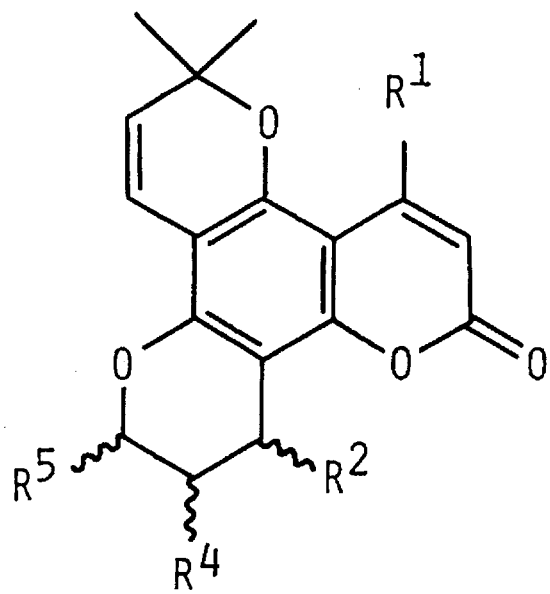
Series 1  FIG. 5A
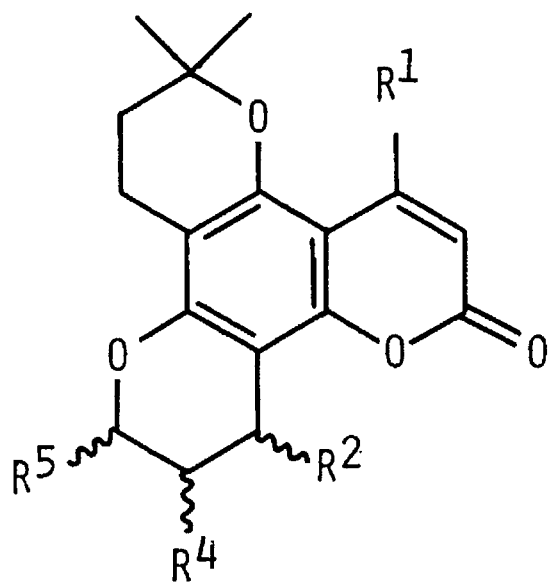
Series 2  FIG. 5B

Dihydrocalanolide A

Dihydrocalanolide B

Dihydrocostatolide

Dihydrosoulattrolide

CALANOLIDE AND RELATED ANTIRETROVIRAL COMPOUNDS, COMPOSITIONS, AND USES THEREOF

This patent application is a continuation-in-part of copending U.S. patent application Ser. No. 07/861,249 filed on Mar. 31, 1992.

TECHNICAL FIELD OF THE INVENTION

This invention relates to antiviral compounds, in particular antiviral compounds isolated from, or derived from compounds isolated from, plants of the genus Calophyllum, specifically compounds referred to as calanolides. This invention also relates to methods of isolating antiviral compounds from Calophyllum plants, compositions comprising calanolides, related compounds, and derivatives thereof, and methods of using the compositions in clinical applications, such as antiviral therapy and the prevention of viral infection.

BACKGROUND OF THE INVENTION

Acquired immune deficiency syndrome (AIDS) is a very serious disease, reported cases of which have increased dramatically within the past several years. Estimates of reported cases in the very near future also continue to rise dramatically. Consequently, there is a great effort to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct types of HIV have been described to date, namely HIV-1 and HIV-2. The acronym HIV will be used herein to refer to HIV viruses generically.

Specifically, HIV is known to exert a profound cytopathic effect on the CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. There are many ways in which an agent can exhibit anti-retroviral activity. For example, HIV requires at least four viral proteins for replication: reverse transcriptase (RT), protease (PR), transactivator protein (TAT), and regulator of virion-protein expression (REV). Accordingly, viral replication could theoretically be inhibited through inhibition of any one or all of the proteins involved in viral replication.

Anti-retroviral agents, such as AZT and ddC, are known to inhibit RT. There also exist anti-viral agents that inhibit TAT.

Nucleoside derivatives, such as AZT, are the only clinically active agents that are currently available for antiviral therapy. Although very useful, the utility of AZT and related compounds is limited by toxicity and insufficient therapeutic indices for fully adequate therapy.

Synthetic peptides also are being developed for potential use as inhibitors of the retroviral protease in the treatment of AIDS. Although these inhibitors are effective in preventing the retroviral protease from functioning, the inhibitors suffer from some distinct disadvantages. First of all, since the active site of the protease is hindered, i.e., has reduced accessibility as compared to the remainder of the protease, the ability of the inhibitors to access and bind in the active site of the protease is impaired. Secondly, the peptide inhibitors that bind to the active site of the protease are generally poorly soluble in water, causing distinct problems in drug delivery.

Therefore, new classes of antiviral agents to be used alone or in combination with AZT and/or other agents are urgently needed for effective antiviral therapy against HIV. New agents, which may be used to prevent HIV infection, are also important.

BRIEF SUMMARY OF THE INVENTION

It is an object of the present invention to provide novel antiviral compounds, in particular antiviral compounds isolated from plants of the genus Calophyllum, specifically compounds referred to as calanolides, related compounds, and derivatives thereof.

It is another object of the present invention to provide a method of isolating novel antiviral compounds, specifically calanolides, related compounds, and derivatives thereof, from plants of the genus Calophyllum, more specifically from *Calophyllum lanigerum* Miq., var. austrocoriaceum (T. C. Whitmore) P. F. Stevens, from *Calophyllum teysmannii* Miq. var inophylloide (King) P. F. Stevens.

It is still another object of the present invention to provide a composition, in particular a pharmaceutical composition, which inhibits the growth or replication of a virus, such as a retrovirus, in particular a human immunodeficiency virus, specifically HIV-1 or HIV-2.

It is an additional object of the present invention to provide a composition, in particular a pharmaceutical composition, which prevents infection of an animal, in particular a human, with a virus, such as a retrovirus, in particular a human immunodeficiency virus, specifically HIV-1 or HIV-2.

Yet another object of the present invention is to provide a method of treating an animal, in particular a human, infected with a virus, such as a retrovirus, in particular a human immunodeficiency virus, specifically HIV-1 or HIV-2.

A further object of the present invention is to provide a method of treating an animal, in particular a human, to prevent infection with a virus, such as a retrovirus, in particular a human immunodeficiency virus, specifically HIV-1 or HIV-2.

These and other objects of the present invention, as well as additional inventive features, will become apparent from the description herein.

The present invention provides novel antiviral compounds, in particular antiviral compounds isolated from, as well as derivatives of compounds isolated from, plants of the genus Calophyllum (particularly, *Calophyllum lanigerum* var. austrocoriaceum and *Calophyllum teysmannii* var. inophylloide), specifically compounds referred to as calanolides, related compounds, and derivatives thereof in substantially pure form. The present invention also provides for a method of isolating and purifying calanolides and related antiviral compounds from Calophyllum plants, in particular from *Calophyllum lanigerum* Miq., and from *Calophyllum teysmannii* Miq. The isolated and derived compounds may be used in a composition, such as a pharmaceutical composition, which may additionally comprise one or more other antiviral agents. Such a composition has been found to inhibit the growth or replication of a virus, in particular a retrovirus, specifically a human immunodeficiency virus, such as HIV-1 or HIV-2. The composition, therefore, is expected to have utility in the therapeutic treatment of an animal, such as a human, infected with a virus, particularly a retrovirus, specifically a human immunodeficiency virus, such as HIV-1 or HIV-2, and in the prophylactic treatment of an animal, such as a human, to prevent viral infection.

BRIEF DESCRIPTION OF THE DRAWINGS

FIG. 2 illustrates previously known structures (compounds 9–4) reported from other sources.

FIG. 4, A–D, shows an example of anti-HIV-1 activity of a calanolide. FIG. 4A depicts the relative numbers of viable CEM-SS cells, as assessed by the BCECF assay; FIG. 4B depicts the relative DNA content of the respective cultures; FIG. 4C depicts the relative numbers of viable CEM-SS cells, as assessed by the XTT assay. In FIGS. 4A, 4B, and 4C, the data points are represented as the percent of the uninfected, non-drug treated control values. In FIG. 4D the data points are represented as the percent infected, non-drug treated control values.

FIGS. 5A and 5B more generally illustrate calanolides and derivatives thereof (series 1) and 7,8-dihydrocalanolides and derivatives thereof (series 2), respectively, wherein $R^1$ is $C_1$–$C_6$ alkyl or aryl; $R^2$ is ◂ OH, ⋯ OH, ◂ $OR^3$, ⋯ $OR^3$, ◂ $O_2CR^3$, ⋯ $O_2CR^3$, ◂ $O_3SR^3$, or ⋯ $O_3SR^3$, wherein $R^3$ is $C_1$–$C_6$ alkyl or aryl; and $R^4$ and $R^5$ are the same or different and are each ◂ $CH_3$ or ⋯ $CH_3$. (The symbol ◂ indicates a bond that extends out of the plane of the paper toward the reader, whereas the symbol ⋯ indicates a bond that extends below the plane of the paper away from the reader.)

Figure 1:
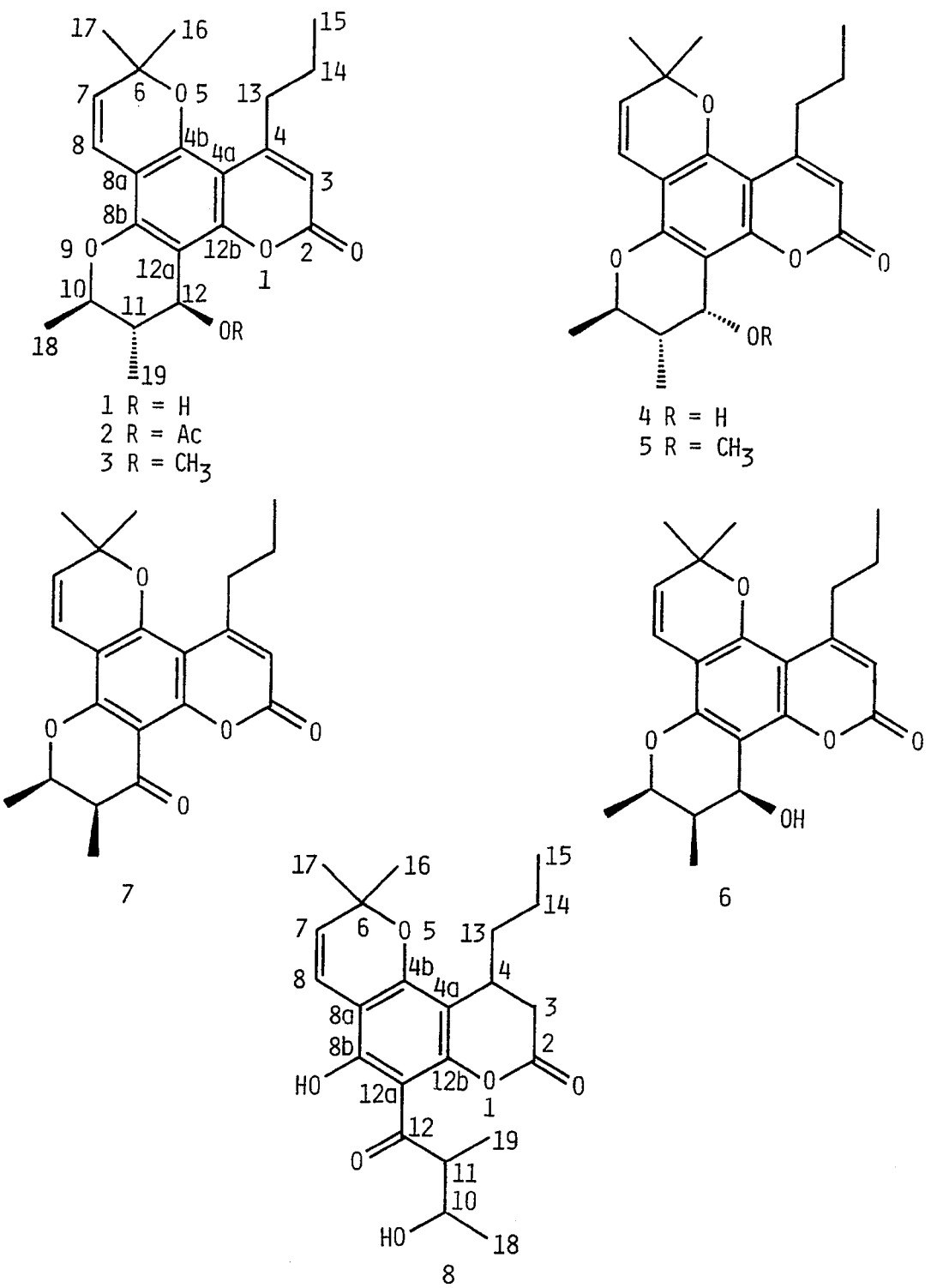
FIG. 1 illustrates the structures of calanolides and related derivatives (compounds 1–8) isolated from *Calophyllum lanigerum* var. austrocoriaceum. Compound 1 is calanolide A, and compound 4 is calanolide B.

By convention with the chemical literature, when only the symbols ◂ or ⋯ are shown within individual chemical structures (e.g., as in FIGS. 1 and 6), they are assumed to be equivalent to ◂ $CH_3$ and ⋯ $CH_3$, respectively.

FIG. 7, A–H, illustrates anti-HIV-1 activities of calanolide A, 7,8-dihydrocalanolide A, calanolide B, 7,8-dihydrocalanolide B, costatolide, 7,8-dihydrocostatolide, soulattrolide, and 7,8-dihydrosoulattrolide, respectively. The effects of a range of concentrations of each compound upon cellular viability was assessed using the XTT assay after 6 days in culture in uninfected CEM-SS cells (o) and in CEM-SS cells infected (●) with HIV-1. The data points are represented as the percent of the uninfected, non-drug treated control values.

DETAILED DESCRIPTION OF THE INVENTION

The present invention provides novel antiviral compounds (hereinafter referred to as "calanolides"), related compounds, and derivatives thereof, in substantially pure form and having the structures and names:

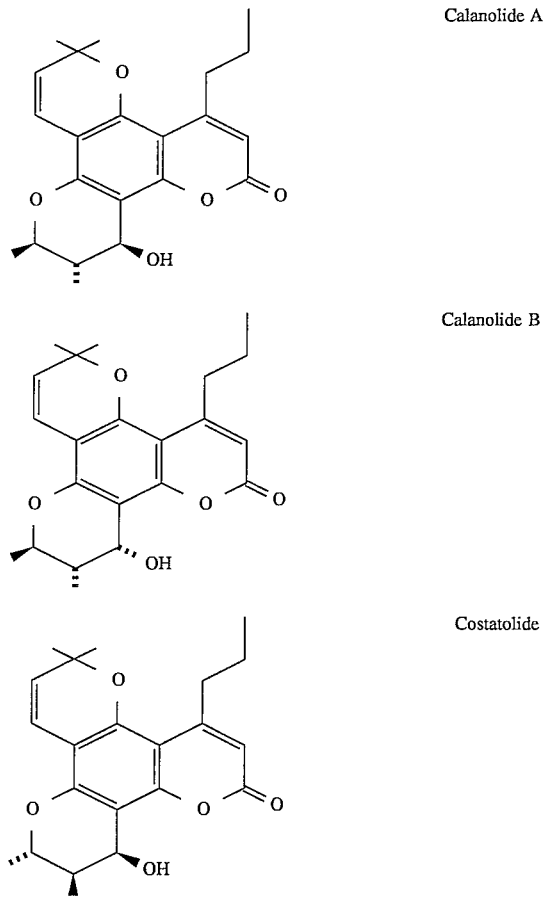

Calanolide A

Calanolide B

Costatolide

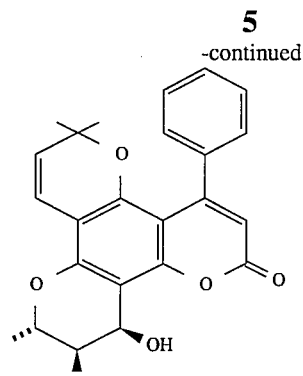

Soulattrolide

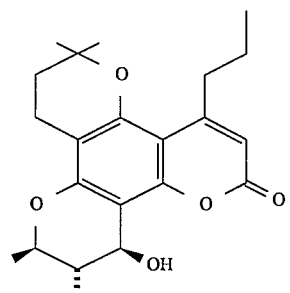

Dihydrocalanolide A

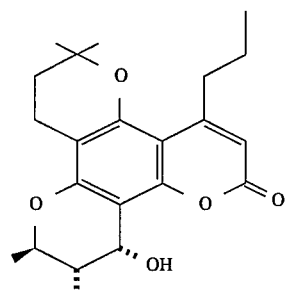

Dihydrocalanolide B

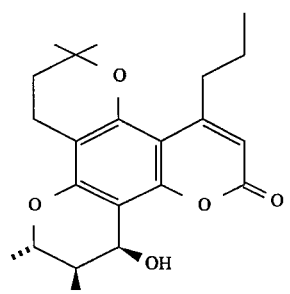

Dihydrocostatolide

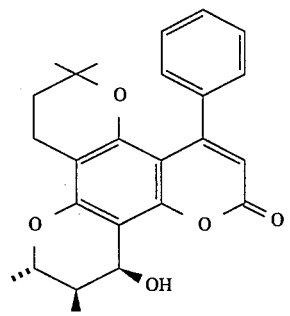

Dihydrosoulattrolide

To the extent the aforesaid compound names are used in the context of describing and claiming the present invention herein, those compound names have reference to the corresponding chemical structures set out immediately above. The antiviral calanolides, related compounds, and derivatives thereof may be described generically as having the structures:

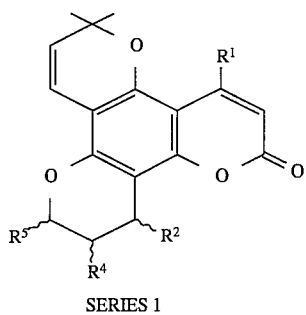

SERIES 1 and

SERIES 2 wherein $R^1$ is $C_1$–$C_6$ alkyl or aryl; $R^2$ is ◂ OH, ⋯ OH, ◂ $OR^3$, ⋯ $OR^3$, ◂ $O_2CR^3$, ⋯ $O_2CR^3$, ◂ $O_3SR^3$, or ⋯ $O_3SR^3$, wherein $R^3$ is $C_1$–$C_6$ alkyl or aryl; $R^4$ and $R^5$ are the same or different and are each ◂ $CH_3$ or ⋯ $CH_3$. While the aryl group may be any suitable aryl substituent, the aryl is preferably a $C_6$–$C_{14}$ ring structure, most preferably phenyl.

The present invention also provides a method of isolating and purifying calanolides and related antiviral compounds and derivatives from plants of the genus Calophyllum, which comprises the steps of:

a) extracting plant material with organic solvents to obtain a crude extract having antiviral activity;

b) solvent-solvent partitioning the crude extract, as necessary, to concentrate an antiviral compound in a non-polar fraction;

c) subjecting the crude extract or the non-polar fraction to gel permeation or vacuum liquid chromatography as necessary to further concentrate the antiviral compound; and, d) isolating and purifying the antiviral compound by HPLC on silica gel and $C_{18}$ reversed-phase columns.

This method is used in conjunction with an antiviral assay to identify the antiviral fractions obtained in the various process steps and may be used to obtain antiviral calanolides, related antiviral compounds, and antiviral derivatives from plant material consisting of leaves, stems, twigs, fruits, flowers, wood, bark, or roots of the said Calophyllum plants. Such antiviral compounds may also be obtained by this method, wherein steps b) and c) may be deleted, from the latex harvested nondestructively from Calophyllum plants.

The antiviral calanolides, related antiviral compounds, and antiviral derivatives thereof, obtained in accordance with the present inventive method, may be used alone or in combination with other antiviral agents in compositions, such as pharmaceutical compositions, to inhibit the growth or replication of a virus, such as a retrovirus, in particular a human immunodeficiency virus, specifically HIV-1 or HIV-2. It is expected that such compositions will have utility in the therapeutic treatment of an animal, in particular a human, infected with one or more of the above-cited viruses and in the prophylactic treatment of an animal, in particular a human, who is at risk for infection with one or more of the same viruses.

Prior to the discovery on which this invention is based, antiviral calanolides and derivatives thereof had not been isolated or described. Methods for isolating such compounds had not been determined. The isolation and chemical structures of related compounds, costatolide and dihydrocostatolide (Stout, G. H., *J. Org. Chem.*, 29, 3604–3609 (1964)) and soulattrolide (Gunasekera, S. P., et al., *J. Chem. Soc. Perkin I*, 1505–1511 (1977)) had previously been reported in the chemical literature; however, no antiviral activity was reported for these compounds. Accordingly, since the antiviral activity of none of these compounds was previously known, the potential use of these compounds in compositions, such as pharmaceutical compositions, in the therapeutic and prophylactic treatment of viral infections in animals, in particular humans, had not been recognized.

General Information

An initial observation that led to the present invention was the antiviral activity of extracts from Calophyllum plants in an anti-HIV screen. The screen is one that has been operated by the U.S. National Cancer Institute since 1988 (see Boyd, M. R., in *AIDS, Etiology, Diagnosis, Treatment and Prevention* (DeVita V. T., Jr., Hellman S., Rosenberg S. A., eds.), pp. 305–319 (Philadelphia: Lippincott, 1988)).

The plant family Guttiferae contains the genus Calophyllum, which is comprised of approximately 187 different species. A brief description of the genus Calophyllum can be found in D. J. Mabberley, "The Plant Book", Cambridge, University Press, 1987, p. 92. The most updated taxonomic revision of the Old World species of the genus has been published by Stevens, P. F., *J. Arnold Arbor.*, 61, 117–699 (1980). Of the 187 known species, 179 are found in the Old World, from the shores of Tropical Africa east to Tahiti in the Pacific, through Madagascar, Sri Lanka, Southeast Asia, New Guinea, and Northern Australia. The greater number of species, however, occur in Indonesia, Malaysia, and the Philippines.

Previous phytochemical studies of the genus Calophyllum had revealed it to be a rich source of secondary metabolites. Xanthones (Dharmaratne, H. R. W., et al., *Phytochemistry*, 25, 1957–1959 (1986); Kumar, V., *Phytochemistry*, 21, 807–809 (1982); Somanathan, R., et al., *J. Chem. Soc. Perkin I*, 2515–1517 (1974)), steroids (Gunasekera, S. P., et al., *J. Chem. Soc. Perkin I*, 2215–2220 (1975)), triterpenes (Gunatilaka, A. A. L., et al., *Phytochemistry*, 23, 323–328 (1984); Dahanayake, M., et al., *J. Chem. Soc. Perkin I*, 2510–2514 (1974)), coumarins (Samaraweera, U. et al *Tetrahedron Lett.*, 22, 5083–5086 (1981); Gautier, J., et al., *Tetrahedron Lett.*, 27, 2715–2718 (1972)), and benzopyrans (Stout, G. H., *J. Org. Chem.*, 33, 4185–4190 (1968)) are among the compounds reported from Calophyllum species; however, no antiviral activity had been previously associated with any compounds from this genus.

A specific bioassay-guided strategy was used to isolate, purify, and identify the individual bioactive compounds from the extracts of Calophyllum plants. In this strategy, decisions concerning the overall chemical isolation method to be applied, and the nature of the individual steps therein, were determined by interpretation of biological testing data. The anti-HIV screening assay (Weislow, O. S., et al., *J. Natl. Cancer Inst.*, 81(8), 577–586 (1989)) used in this process measured the degree of protection of human T-lymphoblastoid cells from the cytopathic effects of HIV. Fractions of the extracts were prepared using a variety of chemical means and were tested blindly in the primary screen. Active fractions were separated further, and the resulting subfractions were tested blindly in the screen. This process was repeated as many times as necessary in order to obtain the active, i.e., antiviral, fraction(s) representing pure compound(s), which then could be subjected to detailed chemical analysis and structure elucidation. In this manner, the new antiviral class of compounds described herein was discovered.

Although *Calophyllum lanigerum* var. austrocoriaceum and *Calophyllum teysmannii* var. inophylloide were used as the principal sources of calanolides and related compounds in the present invention, it will be appreciated that such compounds also may be obtained from other species of the same genus. For example, such other source species may include *Calophyllum lanigerum* var. lanigerum, *Calophyllum teysmannii* var. teysmannii, and *Calophyllum teysmannii* var. bursiculum P. F. Stevens.

Taxonomy

*Calophyllum lanigerum* var. austrocoriaceum. The plant material utilized in Example 2 herein specifically belongs to var. austrocoriaceum of *Calophyllum lanigerum* and was collected by J. S. Burley & B. Lee on Oct. 18, 1987 in Setunggang swamp forest near Batang Kayan River, of the Municipality of Lundu, Sarawak (East Malaysia), at an altitude of 3 m above sea level and at a latitude of 2° N and a longitude of 110° E, under a U.S. National Cancer Institute contract to D. D. Soejarto of the University of Illinois at Chicago. This collection is documented by voucher herbarium specimens Burley & Lee 351, in deposit at the U.S. National Herbarium of the Smithsonian Institution, Washington, D.C. Duplicates of this specimen are also in deposit at the Sarawak Forest Herbarium in Kuching (East Malaysia), the John G. Searle Herbarium of the Field Museum of Natural History, Chicago (Ill.), and the Arnold Arboretum Herbarium of Harvard University in Cambridge (Mass.). The identity of these specimens as *Calophyllum lanigerum* Miq. var. austrocoriaceum (T. C. Whitmore) P. F. Stevens was made by Dr. Peter F. Stevens, Arnold Arboretum of Harvard University, the taxonomic specialist of the genus Calophyllum. Further taxonomic details of the specific plant used in Example 2 are provided in Example 1 below.

*Calophyllum teysmannii* var. inophylloide. The plant material utilized in Example 5 herein specifically belongs to var. inophylloide of *Calophyllum teysmannii*. In March 1992, as part of a field search in an attempt to recollect *Calophyllum lanigerum* var. austrocoriaceum, samples of a Calophyllum species (Soejarto et al. 7605) from a kerangas forest near Sampedi forest reserve, about 50 km west of Kuching, Sarawak, were collected. Anti-HIV tests of extracts from this plant (leaf and twig; stem) showed activity. Dr. Peter F. Stevens of Harvard University, the specialist of Calophyllum, identified this 7605 specimen as *Calophyllum teysmannii* Miq. var. inophylloide (King) P. F. Stevens.

In July 1992, as part of the continuing field search for *Calophyllum lanigerum* var. austrocoriaceum, latex samples of other Calophyllum species were collected, two of which belonging to Soejarto et al. 7853 and 7854 trees also showed anti-HIV activity. The locality of these trees is Sampedi Forest Reserve kerangas forest, separated about 1 km from the locality of 7605, at an altitude of between 30–60 m above sea level. Both 7853 and 7854 trees were marked by an orange plastic ribbon, and numbered using an embossed aluminum plate, affixed to the trees with a nail.

On Jan. 7 and 8, 1993, voucher herbarium specimens and more latex samples were recollected from both trees 7853 and 7854, with the assistance of staff of the Sarawak Forest Department. In addition, further search in the surrounding areas yielded four (4) more trees (Soejarto et al. 7899–7902) of the same species as 7853 and 7854, from which latex samples were also collected. These trees were similarly marked and numbered for future relocation.

When voucher herbarium specimens of Soejarto et al. 7605 were compared with those of 7853, 7854, and 7899–7902, it was apparent that they are all of the same species, namely, *Calophyllum teysmannii* Miq. var. inophylloide (King) P. F. Stevens. A duplicate set of voucher specimens 7853 and 7854 was sent to Dr. Peter F. Stevens on Jan. 17, 1993; on Jan. 19, 1993, Dr. Stevens confirmed the identity of 7853 and 7854 as *Calophyllum teysmannii* var. inophylloide. Further taxonomic details of the specific plants used in Examples 7 and 8 below are provided in Example 6 and Table 3 herein.

Isolation And Purification Of Calanolides And Related Antiviral Compounds From Calophyllum Plants A variety of methods can be used for the chemical isolation of calanolides and related antiviral compounds from Calophyllum plants. Among these methods are extraction, solvent-solvent partitioning, flash- or vacuum-liquid chromatography, gel permeation chromatography, and HPLC, with a variety of bonded phases. The isolation of the pure active compounds can be monitored by UV, TLC, and anti-HIV bioassay. Typical isolation procedures are set forth below for illustrative purposes.

Antiviral calanolides and related antiviral compounds from Calophyllum plant parts. Approximately 0.2 kilogram of air-dried plant material, for example, consisting of leaves, twigs, fruit or bark, is first ground to a fine powder and extracted with 1:1 MeOH-$CH_2Cl_2$; this is followed by a second extraction with methanol. These organic extracts typically amount to a total of about 5–20% of the mass of the starting plant material. The initial crude extract is dissolved in 4:1 MeOH-$H_2O$ and extracted three times with $CCl_4$. The concentrated $CCl_4$ phase is fractionated by either gel permeation on Bio-Beads S-X4 (Bio-Rad Laboratories, Inc.; Richmond, Calif.) or vacuum liquid chromatography on silica gel. The calanolides are then purified from those column fractions that demonstrate HIV-inhibitory activity by sequential HPLC on silica (elution with 3:7 EtOAc-hexane) and $C_{18}$ reversed-phase (elution with 9:1 MeOH-$H_2O$) columns. Using this general procedure, either calanolide A or calanolide B, or both, can be obtained, for example, in an overall yield of about 0.05–0.2%; related compounds also present in the extract can be obtained in similar yields. The isolation of calanolides and derivatives thereof from *C. lanigerum* var. austrocoriaceum is described in greater detail in Example 2.

Antiviral calanolides and related antiviral compounds from latex of Calophyllum plants. A simplified procedure can be used to obtain high yields of antiviral calanolides or related antiviral compounds non-destructively from Calophyllum plants. For example, 10–100 grams of crude Calophyllum plant latex, which can be harvested from Calophyllum plants as described further in Example 7 below, is extracted with $CHCl_3$:MeOH (1:1). The solution is filtered and evaporated to yield a residue typically amounting to 60–70% of the mass of the original latex. The antiviral compounds may then be separated and purified in high yields, typically 10–40% of the total residue mass, by HPLC on silica eluted with hexane:EtOAc (7:3). The isolation of costatolide (compound 9 of FIG. 2) and soulattrolide (compound 14 of FIG. 2) from latex of *Calophyllum teysmannii* var. inophylloide is described more specifically in Example 8 herein.

Rationale and collection of latex from Calophyllum plants. In the process of plant drug discovery and development, after an initial small (0.5–1 kg dry weight) screening-sized sample shows biological activity of interest, and the promising active compound(s) is (are) identified, a larger quantity (10–20 kg dry weight) of material typically must be recollected, in order to permit reisolation of a larger quantity of the pure compound(s) for further preclinical investigation. If the results of the preclinical studies continue to be promising, an even larger quantity of plant material (50–1000 kg dry weight) of that species will need to be recollected for further developmental studies. Very much larger amounts will be required for clinical use. Collection of leaf, twig, stembark, and root samples in large quantities is destructive and may be detrimental to the plant species in question and to the forest environment.

Considering that Calophyllum produces latex, if the latex could be shown to possess the same biological activity, i.e., containing the same anti-HIV compound(s) of interest, it would be most desirable to use the latex as a source (raw) material for re-isolation work and, eventually, for industrial production of the drug. Latex is exuded when a treebark is slashed (cut), and the resinous exudate may be collected periodically, without damage to the tree itself. Examples of such non-destructive harvest methods are provided by the para rubber tree (*Hevea brasiliensis*) and the sugar maple tree (*Acer saccharum*). Such a method is now clearly applicable to the harvest of Calophyllum latex, which can lead to the sustainable or continued utilization of the forest resource.

Latex collections of Calophyllum were initiated on Jul. 19, 1992, in Sarawak; then on Oct. 9, 1992, in the Singapore Garden jungle for *Calophyllum lanigerum* var. austrocoriaceum; and on Oct. 11–13, 1992, again in Sarawak, for various Calophyllum species, including *Calophyllum lanigerum* var. austrocoriaceum. Finally, on Jan. 7–8, 1993, field experiments were run to collect latex samples from trees of *C. teysmannii* var. inophylloide in the Sampedi Forest Reserve. An adequate latex yield was obtained from 5 trees, by collecting latex samples from each of these trees on 3 different occasions during a total period of 2 days (Jan. 7–8, 1993). A fourth collection from the same trees was done on the following week of January 11, 1993. Approximately 100 grams of latex was initially obtained. Example 7 below sets forth in further detail the non-destructive harvest of latex from *Calophyllum tyesmannii* var. inophylloide; Example 8 illustrates the isolation and purification of calanolide-related antiviral compounds, costatolide and soulattrolide, from such latex. Based on the fact that latex scraped from 6-month old wounds that had healed still showed the presence of costatolide on the TLC plates, and the fact that 3 scraping operations on the same slashes on a tree could be made in different occasions, each of which yielded an appreciable latex quantity, it is apparent that latex harvest is a sustainable harvest method.

Determination Of Chemical Structures Of Antiviral Calanolides And Related Antiviral Compounds From Calophyllum Plants Chemical structures of calanolides and related compounds and derivatives thereof which can be isolated by the above general procedure from extracts from Calophyllum plants are shown in FIG. 1. The proofs of the structures can be obtained by a combination of methods, including primary spectral analyses (e.g., high-resolution NMR and mass spectrometry, infrared and UV spectroscopy), comparisons of spectral and physicochemical properties with related literature precedents, and by selected derivatization procedures, such as for determination of absolute stereochemistry. The structure proofs for calanolides A, B, and derivatives thereof from *C. lanigerum* var. austrocoriaceum are described in detail in Example 3 and summarized in Tables 1 and 2.

It will be appreciated by one who is skilled in the art that antiviral calanolides, related antiviral compounds, and derivatives thereof, other than those specifically described herein, may be isolated from other Calophyllum species and other natural sources and that such antiviral calanolides, related antiviral compounds, and derivatives thereof also may be synthesized chemically. Generic structural series, designated as "Series 1" and "Series 2," are described in detail in Example 5 and FIGS. 5A and 5B, respectively. Members of series 1 can be converted to the corresponding 7,8-dihydro compounds of series 2, by catalytic hydrogenation. Example 9 below more specifically illustrates the preparation of antiviral compounds 7,8-dihydrocalanolide A, 7,8-dihydrocalanolide B, 7,8-dihydrocostatolide, and 7,8-dihydrosoulattrolide; the structures of these compounds are shown in FIGS. 6 A–D.

Antiviral Activity

The antiviral activity of calanolides and related compounds and derivatives thereof can be demonstrated further in a series of interrelated in vitro assays (Gulakowski, R. J., et al., *J. Virol. Methods,* 33, 87–100 (1991)), which accurately predict antiviral activity of chemical compounds in humans. These assays measure the ability of compounds to prevent the replication of HIV and/or the cytopathic effects of HIV on human target cells. These measurements directly correlate with the pathogenesis of HIV-induced disease in vivo. Accordingly, the results of the analysis of the antiviral activity of calanolides and related compounds and derivatives thereof from *C. lanigerum,* as set forth in Example 3 and as illustrated in FIGS. 4 A–D and FIGS. 7 A–H, are believed to predict accurately the antiviral activity of these compounds in humans.

The compounds which are the subject of the present invention can be shown to inhibit a retrovirus, such as the human immunodeficiency virus, specifically HIV-1 and HIV-2. As one skilled in the art will appreciate, the compounds of the present invention probably will inhibit other retroviruses and may inhibit viruses, other than retroviruses. Examples of viruses that may be treated in accordance with the present invention include, but are not limited to, Type C and Type D retroviruses, HTLV-1, HTLV-2, HIV, FLV, SIV, MLV, BLV, BIV, equine infectious, anemia virus, avian sarcoma viruses, such as rous sarcoma virus (RSV), hepatitis type A, B, non-A, and non-B viruses, herpes viruses, cytomegaloviruses, influenza viruses, arboviruses, varicella viruses, measles, mumps and rubella viruses.

Compositions And Formulations

The calanolides and related compounds and derivatives thereof may be formulated into various compositions for use in therapeutic and prophylactic treatment methods. The present inventive composition may be used to treat a virally infected animal, such as a human. The compositions of the present invention are particularly useful in inhibiting the growth or replication of a virus, such as a retrovirus, in particular a human immunodeficiency virus, specifically HIV-1 and HIV-2. The compositions also are expected to be useful in the treatment of animals, such as humans, infected with other viruses, such as those listed above. Furthermore, such compositions should find utility in the prophylactic treatment of animals, such as humans, who are at risk for viral infection.

Compositions for use in the prophylactic or therapeutic treatment methods of the present invention comprise one or more calanolides or related compounds and derivatives thereof and a pharmaceutically acceptable carrier. Pharmaceutically acceptable carriers are well-known to those who are skilled in the art, as are suitable methods of administration. The choice of carrier will be determined in part by the particular calanolide compound, as well as by the particular method used to administer the composition.

One skilled in the art will appreciate that various routes of administering a drug are available and, although more than one route may be used to administer a particular drug, a particular route may provide a more immediate and more effective reaction than another route. Furthermore, one skilled in the art will appreciate that the particular pharmaceutical carrier employed will depend, in part, upon the particular compound employed and the chosen route of administration. Accordingly, there is a wide variety of suitable formulations of the composition of the present invention.

Formulations suitable for oral administration may consist of liquid solutions, such as an effective amount of the compound dissolved in diluents, such as water, saline, or orange juice; capsules, sachets or tablets, each containing a predetermined amount of the active ingredient, as solids or granules; solutions or suspensions in an aqueous liquid; and oil-in-water emulsions or water-in-oil emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

The calanolides and related compounds and derivatives thereof, alone or in combination with other antiviral compounds, can be made into aerosol formulations to be administered via inhalation. These aerosol formulations can be placed into pressurized acceptable propellants, such as dichlorodifluoromethane, propane, nitrogen, and the like.

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

Formulations for rectal administration may be presented as a suppository with a suitable base comprising, for example, cocoa butter or a salicylate.

Formulations suitable for vaginal administration may be presented as pessaries, tampons, creams, gels, pastes, foams, or spray formulas containing, in addition to the active ingredient, such carriers as are known in the art to be appropriate. Similarly, the active ingredient may be combined with a lubricant as a coating on a condom.

Formulations suitable for parenteral administration include aqueous and non-aqueous, isotonic sterile injection solutions, which may contain anti-oxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. The formulations may be presented in unit-dose or multi-dose sealed containers, such as ampules and vials, and may be stored in a freeze-dried (lyophilized) condition requiring only the addition of the sterile liquid carrier, for example, water, for injections, immediately prior to use. Extemporaneous injection solutions and suspensions may be prepared from sterile powders, granules, and tablets of the kind previously described.

The dose administered to an animal, particularly a human, in the context of the present invention should be sufficient to effect a prophylactic or therapeutic response in the infected individual over a reasonable time frame. The dose will be determined by the strength of the particular antiviral compound employed, the severity of the disease state, as well as the body weight and age of the infected individual. The size of the dose also will be determined by the existence of any adverse side effects that may accompany the particular compound employed. It is always desirable, whenever possible, to keep adverse side effects to a minimum.

The dosage may be in unit dosage form, such as a tablet or capsule. The term "unit dosage form" as used herein refers to physically discrete units suitable as unitary dosages for human and animal subjects, each unit containing a predetermined quantity of a calanolide or related compound or derivative thereof, alone or in combination with other antiviral agents, calculated in an amount sufficient to produce the desired effect in association with a pharmaceutically acceptable diluent, carrier, or vehicle.

The specifications for the unit dosage forms of the present invention depend on the particular compound or compounds employed and the effect to be achieved, as well as the pharmacodynamics associated with each compound in the host. The dose administered should be an "antiviral effective amount" or an amount necessary to achieve an "effective level" in the individual patient.

Antivral Therapy

Since the "effective level" is used as the preferred endpoint for dosing, the actual dose and schedule may vary, depending upon interindividual differences in pharmacokinetics, drug distribution, and metabolism. The "effective level" may be defined, for example, as the blood or tissue level desired in the patient that corresponds to a concentration of one or more calanolides, or related compounds or derivatives thereof, which inhibits a virus such as HIV in an assay known to predict for clinical antiviral activity of chemical compounds. The "effective level" for compounds which are the subject of the present invention also may vary when the compositions of the present invention are used in combination with AZT or other known antiviral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it may be desirable to utilize a "mega-dosing" regimen, wherein a large dose of the calanolide or derivative thereof is administered, time is allowed for the compound to act, and then a suitable reagent is administered to the individual to inactivate the calanolide or derivative thereof.

The pharmaceutical composition may contain other pharmaceuticals, in conjunction with the calanolide or related compound or derivative thereof, when used to therapeutically treat acquired immunodeficiency syndrome (AIDS). Representative examples of these additional pharmaceuticals include antiviral compounds, immunomodulators, immunostimulants, and antibiotics. Exemplary antiviral compounds include 3'-azido-2',3'-dideoxythymidine (AZT), 2'3'-dideoxyinosine (ddI), 2'3'-dideoxycytidine (ddC), 2'3'-didehydro-2'3'-dideoxythymidine (D4T), 9-(1,3-dihydroxy-2-propoxymethyl)guanine (gancyclovir), fluorinated dideoxynucleotides such as 3'-fluoro-2'3-dideoxythymidine, nonnucleoside compounds such as 6,11-dihydro-11-cyclopropyl-4-methyldipyrido[2,3-b:2',3'-e][1,4]diazepin-6-one (nevirapine) (Shih et al., PNAS, 88, 9878–9882 (1991)), TIBO and analogs and derivatives such as (+)-S,4,5,6,7-tetrahydro-9-chloro-5-methyl-6-(3-methyl-2-butenyl)-imidazo[4,5,1-jk][1,4]-benzodiazepin-2(1H)-thione (R82913) (White et al., *Antiviral Research,* 16, 257–266 (1991)), Ro 31-8959 (Craig et al., *Antiviral Research,* 16, 295–305 (1991)), BI-RJ-70 (Shih et al., supra), 9-(2-hydroxyethoxymethyl)guanine (acyclovir), α-interferon, recombinant CD4 (Merigan et al., *The American Journal of Medicine,* 90 (Suppl. 4A), 8S-17S (1991)), pyridine analogs such as (3-[(benzoxazol-2-yl)ethyl]-5-ethyl-6-methylpyridin-2(1H)-one (L-696,229), 1-[(2-hydroxyethoxy)methyl]-6-phenylthiothymine (HEPT), carbocyclic 2',3'-didehydro-2',3'-dideoxyguanosine (carbovir), and [2',5'-Bis-O-(tert-butyldimethylsilyl)-β-D-ribofuranosyl]-3'-spiro-5"-(4"-amino-1",2"-oxathiole-2",2"-dioxide)thymine (TSAO-T). Exempletive immunomodulators and immunostimulants include various interleukins, CD4, cytokines, antibody preparations, blood transfusions, and cell transfusions. Exempletive antibiotics include antifungal agents, antibacterial agents, and anti-*Pneumocystis carinii* agents.

Administration of the inhibitory compound with other anti-retroviral agents and particularly with known reverse transcriptase (RT) inhibitors, such as ddC, AZT, ddI, ddA, or other inhibitors that act against other HIV proteins, such as anti-TAT agents, will generally inhibit most or all replicative stages of the viral life cycle. The dosages of ddC and AZT used in AIDS or ARC patients have been published. A virustatic range of ddC is generally between 0.05 $\mu$M to 1.0 $\mu$M. A range of about 0.005–0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently 0.01 mg/kg body weight ddC given every 8 hours is preferred. When given in combined therapy, the other antiviral compound, for example, may be given at the same time as the calanolide compound or the dosing may be staggered as desired. The two drugs also may be combined in a composition. Doses of each may be less when used in combination than when either is used alone.

EXAMPLES

The present inventive compounds and methods are further described in the context of the following examples. These examples serve to illustrate further the present invention and are not intended to limit the scope of the invention.

Example 1

This example sets forth more specifically the taxonomic characteristics of the *Calophyllum lanigerum* var. austrocoriaceum specimen (Burley & Lee 351) used in example 2: tree about 8 m tall, dbh (diameter at breast high) 15 cm; bark light brownish with dark brown longitudinal rows of lenticels, inner bark red, underbark orange; twigs somewhat flattened and more-or-less angled, dark brown and covered with short trichomes of the same color, terminal buds plump, 1.5–2 cm long, thickish, beset with rusty brown, soft-tomentose pubescence; leaves coriaceous, blades narrowly ovate to oblong, 7–17 cm long, 3–5 cm wide, chestnut brown in dry state, latex canals as prominent as veins, about 10 veins per 5 mm, petiole 1–1.5 cm long; inflorescence few-flowered (3–5 flowers per inflorescence), axis 3–3.5 cm long, lowest internode 0.5–1 cm long; fruits young, globose to ellipsoid, 0.5–1 cm across, green in fresh condition, dark chestnut brown when dry.

Example 2

This example illustrates the isolation of calanolides and derivatives thereof from extracts of *Calophyllum lanigerum* var. austrocoriaceum. Dried fruit and twigs (763 g) of *Calophyllum lanigerum* var. austrocoriaceum were stored at −20° until the material was ground, percolated in 1:1 $CH_2Cl_2$/MeOH, and washed with 100% MeOH. Removal of the solvent under reduced pressure provided 72.5 g of organic extract.

A 10 g portion of the organic extract was subjected to a solvent-solvent partitioning protocol. A 10 g portion of the organic extract was suspended in 500 ml $CH_3OH$—$H_2O$ (9:1) and extracted with hexane (3×300 ml). The water content of the polar phase was increased to 20%, whereupon a second extraction was conducted with $CCl_4$ (3×300 ml). The anti-HIV activity of all fractions was assessed using a routine primary screening assay (Weislow, O. S., et al., *J. Natl. Cancer Inst.*, 81(8), 577–586 (1989)) at each chromatographic step. Anti-HIV activity was concentrated in the hexane (770 mg) and $CCl_4$ (590 mg) soluble fractions. The active fractions were individually separated by vacuum liquid chromatography (VLC) on 10 g of silica gel using mixtures of hexane/EtOAc. The active constituents that eluted with 10–25% EtOAc were combined, based upon TLC and $^1H$ NMR profiles, to provide two active fractions. The individual fractions were further separated by VLC on silica, using gradual step-gradient elution with hexane/ EtOAc mixtures. Final purification gave eight compounds (1–8), the structures of which are given in FIG. 1. Silica HPLC eluted with 7:3 hexane/EtOAc gave calanolide A (1) (11.7 mg), calanolide B (4) (5.0 mg), and compound 7 (12.5 mg). Purification of the other components was effected by $C_{18}$ HPLC with 9:1 MeOH/$H_2O$ to give 12-acetoxycalanolide A (2) (7 mg), 12-methoxycalanolide A (3) (5 mg), 12-methoxycalanolide B (5) (16 mg), compound 6 (4 mg), and compound 8 (11 mg). FIG. 2 shows six related structures (9–14) previously reported from other sources. By comparing the structures and the spectral and physicochemical properties of the novel compounds of FIG. 1 with those of the known compounds of FIG. 2, it can be seen that the compounds 1–8 of the present invention differ from those compounds previously reported from other sources.

Example 3

This example sets out the structure proofs for calanolides A and B and related derivatives from *Calophyllum lanigerum* var. austrocoriaceum, which were obtained in Example 1. Calanolide A (1) was isolated as an optically active oil, $[\alpha]_D$=+60°, which gave a HREIMS parent ion at m/z 370.1764 daltons, indicating a molecular formula of $C_{22}H_{26}O_5$. The mass spectrum contained significant fragment ions for $M^+$—$CH_3$ (m/z 355, 100%), $M^+$—$CH_3$—$H_2O$ (m/z 337, 12%) and $M^+$—$C_5H_{11}$ (m/z 299, 29%). The infrared spectrum showed bands corresponding to hydroxyl (3300 cm$^{-1}$) and carbonyl (1735 cm$^{-1}$) groups. Resonances for 11 sp$^2$ carbons in the $^{13}C$ NMR spectrum revealed a conjugated ester (δ 160.4), a disubstituted olefin conjugated to a phenyl group (δ 126.9 [1H] and 116.5 [1H]), a trisubstituted olefin conjugated to a carbonyl (δ 158.9 and 110.1 [1H]), and a fully substituted benzene ring bearing three oxygen moieties (δ 154.5, 153.1, 151.1, 106.3, 106.4, and 104.0). Taking into account the number of double bond equivalents implicit in the molecular formula, calanolide A (1) was determined to be tetracyclic. The $^1H$ NMR spectrum showed two methyl singlets (δ 1.49 and 1.44), two methyl doublets (δ 1.44 and 1.13), and a methyl triplet (δ 1.01). Additional proton signals included those of an allylic methylene (δ 2.87 [2H], m), an aliphatic methylene (1.63 [2H], m), and three olefin protons (δ 6.60 d, J=9.5 Hz; 5.92 t, J=1.0 Hz; 5.52 d, J=9.5 Hz). These data suggested that calanolide A (1) was a coumarin derivative related to costatolide (9), a metabolite previously reported from *Calophyllum costatum* (Stout, G. H., *J. Org. Chem.*, 29, 3604–3609 (1964)).

One-bond and long-range proton detected heteronuclear correlation experiments (HMQC and HMBC) allowed the complete assignment of both the $^1H$ NMR (Table 1) and $^{13}C$ NMR spectra (Table 2) of calanolide A (1). Key correlations included those between H8 and carbons 4b, 6, 8a, and 8b, which helped to establish the position of the 2,2-dimethylchromene system. Placement of the n-propyl group at C4 was aided by a 1.0 Hz allylic coupling between the C13 allylic methylene protons and the C3 olefin proton, and by three-bond heteronuclear correlations from the C13 methylene protons to C3 and C4a. The remaining substitution pattern about the coumarin nucleus was defined by correlations between H12 and carbons 8b, 10, 11, 12a, 12b, and 19. This confirmed that, although calanolide A (1) had the same skeleton as costatolide (9), they differed in the relative stereochemistry of their substituents about the 2,3-dimethylchromanol ring.

In the $^1H$ NMR spectrum of compound 1, the H12 benzylic carbinol proton showed a 8.0 Hz coupling to H11, which revealed that these two protons had a trans-diaxial orientation. A 9.0 Hz coupling between H11 and H10 established that H10 also was axial. This assignment was supported by nOe enhancements (3%) observed between the diaxial H10 and H12 protons. Calanolide A (1) was thus determined to be a diastereomer of costatolide (9), which showed $J_{10-11}$ and $J_{11-12}$ of 10.5 Hz and 3.5 Hz, respectively (Stout, G. H., et al., *J. Org. Chem.*, 29, 3604–3609 (1964)). Two related coumarin derivatives, inophyllum B (10) (Bandara, B. M. R., et al., *Phytochemistry*, 25(2), 425–428 (1986)) and cordatolide A (11) (Dharmaratne, H. R. W., et al., *Phytochemistry*, 24, 1553–1557 (1985)) reportedly have the same relative stereochemical features about the chromanol ring as those found in compound 1, but differ in their C4 substituents. The $J_{10-11}$ and $J_{11-12}$ coupling constants observed in calanolide A (1) agree closely with those described in the above-cited publications for compounds 10 and 11.

Other physicochemical and spectral data for calanolide A (1) were as follows, $[\alpha]_D$+60° (CHCl$_3$, c 0.7); UV $\lambda_{max}$ (MeOH) 325 (ε 13,700), 284 (ε 22,800), 228 (ε 22,200) nm; IR (film) $\nu_{max}$ 3300, 2966, 1735, 1713, 1583, 1111 cm$^{-1}$; HREIMS obs. m/z 370.1764, calc'd for $C_{22}H_{26}O_5$, 370.1780; low res. MS m/z 370 (38%), 355 (100%), 337 (12%), 299 (29%).

12-Acetoxycalanolide A (2), $[\alpha]_D$=+20°, gave a parent ion by HREIMS at m/z 412.1825 daltons corresponding to a molecular formula of $C_{24}H_{28}O_6$. Significant fragment ions were observed for $M^+$—$CH_3$ (m/z 397, 41%) $M^+$—AcOH (m/z 352 30%) and $M^+$—AcOH—$CH_3$ (m/z 337, 100%). The presence of an acetate group was suggested by a sharp 3H singlet in the $^1H$ NMR spectrum at δ 2.10 and $^{13}C$ NMR resonances at δ 21.2 (3H) and 170.7. The remaining $^1H$ and $^{13}C$ NMR signals for compound 2 were very similar to those recorded for calanolide A (1), except that the H12 resonance in compound 2 was shifted downfield to δ 5.97. This suggested that compound Z was the 12-acetoxy derivative of calanolide A (1). The $J_{10-11}$ (6.5 Hz) and $J_{11-12}$ (6.0 Hz) couplings in compound 2 supported a pseudoaxial orientation of the chromanol ring protons. The slightly diminished chromanol proton couplings in compound 2 conceivably resulted from a slight twisting of the flexible chromanol ring. Further evidence for the proposed substituent configuration was provided by difference nOe enhancements of 2% measured between H10 and H12.

Other physicochemical and spectral data for compound 2 were as follows: $[\alpha]_D$+20° (CHCl$_3$, c 0.5); IR (film) $\nu_{max}$ 2960, 1738, 1585, 1376, 1230, 1138 cm$^{-1}$; HREIMS obs. m/z 412.1825, calc'd for $C_{24}H_{28}O_6$, 412.1886; low res. MS m/z 412 (13%), 397 (41%), 352 (30%), 337 (100%), 299 (8%).

The HREIMS of 12-methoxycalanolide A (3), $[\alpha]_D$=+32°, showed a parent ion at m/z 384.1924 daltons, corresponding to a molecular formula of $C_{23}H_{28}O_5$. Significant fragment ions observed for M$^+$—CH$_3$ (m/z 369, 12%), M$^+$—CH$_3$OH (m/z 352, 9%) and M$^+$—CH$_3$OH—CH$_3$ (m/z 337, 100%) suggested the presence of a methoxyl group, which was confirmed by a $^1$H NMR singlet (δ 3.59, 3H) and a corresponding carbon resonance at δ 57.6. The $^1$H and $^{13}$C NMR spectra revealed that compound 3 had the same skeleton as calanolide A (1). However, important differences were observed in the signals for some of the chromanol ring substituents. In addition to the vicinal couplings of $J_{10-11}$ (3.5 Hz) and $J_{11-12}$ (3.7 Hz), a W coupling of 1.3 Hz was observed between H10 and H12 in compound 3. The W coupling required a pseudodiequatorial configuration for the C10 and C12 protons. Significant nOe enhancements between H11 and both the C10 methyl group (3.5%) and the C12 methoxyl group (3.5%) indicated that H11 was cis to these two substituents and, therefore, had an equatorial orientation about the chromanol ring. It appeared that, in 12-methoxycalanolide A (3), the preferred conformation of the chromanol ring was inverted relative to calanolide A (1). Thus, while H10, H11, and H12 were oriented α, β, α respectively in both compounds, in calanolide A (1) all three protons were axial, and in 12-methoxycalanolide A (3) they were all equatorial.

Other physicochemical and spectral data for compound 3 were as follows: $[\alpha]_D$+32° (CHCl$_3$, c 0.8); IR (film) $\nu_{max}$ 2960, 1731, 1584, 1380, 1137, cm$^{-1}$; HREIMS obs. m/z 384.1924, calc'd for $C_{23}H_{28}O_5$, 384.1937; low res. MS m/z 384 (5%), 369 (12%), 352 (9%), 337 (100%).

Calanolide B (4), $[\alpha]_D$=+8°, was isomeric to calanolide A (1), as it also showed a HREIMS parent ion at m/z 370.1747 daltons, corresponding to $C_{22}H_{26}O_5$. The $^1$H and $^{13}$C NMR spectra of calanolide B (4) were virtually identical to those from calanolide A (1), with the exception of some variations in signals from the chromanol ring. It was clear from the spectral data that compound 4 differed from compound 1 only in the stereochemical disposition of the chromanol ring substituents. Proton-proton coupling constant analysis showed a 10.5 Hz $J_{10-11}$ coupling and a 3.3 Hz $J_{11-12}$ coupling. Thus, H10 and H11 were trans-diaxial while H11 and H12 were in a cis configuration with H12 in a pseudoequatorial orientation. Calanolide B (4) had the same relative stereochemistry as costatolide (9) but its optical rotation was opposite in sign to that reported for compound 9 (Stout, G. H., et al., J. Org. Chem., 29, 3604–3609 (1964)); therefore, compounds 4 and 9 are enantiomeric.

Other physicochemical and spectral data for calanolide B (4) were as follows: $[\alpha]_D$+10° (acetone, c 1.0) UV $\nu_{max}$ (MeOH) 325 (ε 13,700), 284 (ε 22,800), 228 (ε 22,200) nm; IR (film) $\nu_{max}$ 3470, 2970, 1732, 1587 cm$^{-1}$; HREIMS obs. m/z 370.1747, calc'd for $C_{22}H_{26}O_5$, 370.1780; low res. MS m/z 370 (3%), 355 (100%), 337 (13%), 300 (5%), 299 (20%).

12-Methoxycalanolide B (5), $[\alpha]_D$=+34°, provided a HREIMS parent ion at m/z 384.1890 daltons appropriate for a molecular formula of $C_{23}H_{28}O_5$. Additional fragment ions were seen for M$^+$—CH$_3$ (m/z 369, 12 %), M$^+$—CH$_3$OH (m/z 352, 13%) and M$^+$—CH$_3$OH—CH$_3$ (m/z 337, 100%). The $^1$H and $^{13}$C NMR spectra of compound 5 were virtually identical to those recorded for compound 4, with the addition of a sharp 3H singlet at δ 3.58 and a corresponding carbon resonance at δ 59.4. These data indicated that compound 5 was the 12-methoxyl derivative of calanolide B (4). This assignment was confirmed by acid hydrolysis of 2 mg of compound 5 in 400 µl of THF/H$_2$O and 8 µl of 6N HCl at room temperature for 48 hr to provide compound 4 as the only product.

Other physicochemical and spectral data for compound 5 were as follows: $[\alpha]_D$+34° (CHCl$_3$, c 0.5); IR (film) $\nu_{max}$ 2966, 1734, 1716, 1700, 1558, 1540, 1506, 1457 cm$^{-1}$; HREIMS obs. m/z 384.1890, calc'd for $C_{23}H_{28}O_5$, 384.1937; low res. MS m/z 384 (4%), 369 (12%), 352 (13%), 337 (100%).

Compound 6, $[\alpha]_D$=+68°, also was isomeric with calanolide A (1), since it showed similarly a HREIMS parent ion at m/z 370.1695 daltons, consistent with a molecular formula of $C_{22}H_{26}O_5$. Fragment ions were found at M$^+$—CH$_3$ (m/z 355, 100%), M$^+$—CH$_3$—H$_2$O (m/z 337, 25%) and M$^+$—C$_5$H$_{11}$ (m/z 299, 35%) Again the only notable differences between the $^1$H and $^{13}$C NMR spectra of 6 and those recorded for compound 1 were the resonances associated with the chromanol ring. The $J_{10-11}$ in compound 6 was 2.5 Hz, while $J_{11-12}$ was 6.0 Hz. These coupling constants were insufficient to define the relative stereochemistry of carbons 10, 11, and 12. However, the C12 hydroxyl proton gave a sharpened peak with a 1.5 Hz coupling to H12 which suggested that the rate of exchange of the OH proton was reduced due to hydrogen bonding to O1. Hydrogen bonding to O1 would require an equatorial OH at C12. A 5% nOe enhancement between H10 and H12 confirmed that these protons each had axial orientations. Therefore, H11 had to be equatorial. Compound 6 was thus the C11 epimer of calanolide A (1) and had the same substitution pattern and relative stereochemistry about the chromanol ring as the previously described coumarin derivative inophyllum A (12) (Bandara, B. M. R., et al., Phytochemistry, 25, 425–428 (1986)); the $J_{10-11}$ (3.3 Hz) and $J_{11-12}$ values (5.4 Hz) reported earlier for compound 12 were in good agreement with the respective couplings observed in compound 6.

Other physicochemical and spectral data for compound 6 were as follows: $[\alpha]_D$+68° (CHCl$_3$, c 0.7); IR (film) $\nu_{max}$ 2960, 1729, 1620, 1582, 1120 cm$^{-1}$; HREIMS obs. m/z 370.1695, calc'd for C22H26O$_5$, 370.1780; low res. MS m/z 370 (52%), 355 (100%), 337 (25%), 200 (35%).

Compound 7, $[\alpha]_D$=+60°, provided a HREIMS molecular ion at m/z 368.1213 appropriate for a molecular formula of $C_{22}H_{24}O_5$. This required that compound 7 had one additional unsaturation equivalent relative to calanolide A (1). The infrared spectrum, with bands at 1734 and 1697 cm$^{-1}$ suggested the presence of an additional carbonyl group. Heteronuclear correlation experiments allowed the complete assignment of the $^1$H and $^{13}$C NMR spectra of compound 7. While the $^{13}$C NMR spectrum of compound 7 was quite similar to that of calanolide A (1), the C12 peak in compound 7 was shifted downfield to δ 192.9, indicative of an α,β-unsaturated ketone functionality. A shift of the C11 proton resonance in compound 7 to δ 2.61 supported its placement a to a ketone carbonyl.

The small coupling measured between H10 and H11 ($J_{10-11}$=3.0 Hz) indicated that at least one of these protons was equatorial. The previously described oxidation product (13) of soulattrolide (14) (Gunasekera, S. P., et al., *J. Chem. Soc. Perkin I*, 1505–1511 (1977)) contains a similar 2,3-dimethyl-benzopyranone ring system. In compound 13, H10 and H11 are trans, and a $J_{10-11}$ coupling of 11.0 Hz was reported. This indicated that when the H10 and H11 protons were trans, the ring adopted a conformation with these two protons in a diaxial orientation. Therefore, the relative stereochemistry of the H10 and H11 protons in compound 7 had to be cis. The absolute stereochemistry at C10 and C11 has not been determined and, therefore, both of the corresponding methyls have been drawn arbitrarily as α in FIG. 1.

Other physicochemical and spectral data for compound 7 were as follows: $[\alpha]_D$+60° (CHCl$_3$, c 0.5); IR (film) $v_{max}$ 2960, 1734, 1697, 1684, 1575, 1558 cm$^{-1}$; HREIMS obs. m/z 368.1213, calc'd for C$_{22}$H$_{24}$O$_5$, 368.1624; low res. MS m/z 368 (25%), 353 (100%), 297 (68%).

Compound 8, $[\alpha]_D$=+30° had a molecular formula of C$_{22}$H$_{28}$O$_6$, as indicated by the HREIMS parent ion at m/z 388.1890 daltons Fragment ions appropriate for M$^+$—CH$_3$ (m/z 373, 100%), M$^+$—C$_3$H$_7$ (m/z 345, 3%), M$^+$—CO$_2$CH$_3$ (m/z 329, 5%), M$^+$—C$_3$H$_7$O$_2$ (m/z 313, 3%) and M$^+$—COCHCH$_3$CHOHCH$_3$ (m/z 287, 3%) were also observed. The complete $^1$H and $^{13}$C NMR spectra of compound 8 were assigned with information provided from nOe experiments and heteronuclear correlations. The $^{13}$C NMR spectrum contained signals for an unsaturated ketone (δ 201.0), a saturated ester (δ 178.6), a disubstituted olefin (δ 125.6 [1H] and 115.6 [1H]) and a fully substituted benzene ring bearing three oxygens (δ 160.0 [2C], 157.3, 108.9, 102.6 and 101.2). Therefore, compound 8 had only three of the four rings found in the other members of the calanolide series. In contrast to compounds 1–7, which gave vivid blue spots on TLC when charred with vanillin/H$_2$SO$_4$, compound 8 gave a brownish-green spot.

The $^1$H and $^{13}$C NMR spectra of compound 8 showed some resonances that corresponded closely to the coumarin and 2,2-dimethylchromene ring systems of compounds 1–7. However, the C3/C4 double bond in compounds 1–7 was fully saturated in compound 8. For clarity of discussion, as depicted in FIG. 2, the carbon atoms have been numbered in compound 8 in a scheme that is analogous to the numbering shown for calanolide A (1) and which likewise applies to the others of the series, i.e., compounds 2–7. The saturation of the double bond resulted in a methylene (δ 2.81 dd, J=15.0, 9.0 Hz and 2.67 dd, J=15.0, 6.5 Hz) α to the lactone carbonyl that was coupled to the C4 benzylic methine (δ 3.67 m). The C4 proton also showed heteronuclear correlations to C2, C3, C4a, C12b, C13 and C14, which supported the presence of a 3,4-dihydrocoumarin skeleton with an n-propyl substituent at C4. Heteronuclear correlations, including those between H8 and C4b, C6, and C8b, confirmed the placement of the chromene functionality on the coumarin ring system. This suggested that the chromanol ring system present in compounds 1∂14 was open in compound 8.

The position of the phenol on C8b was established by heteronuclear correlations from the phenolic proton to C8a, C8b, and C12a and an nOe interaction with H8. Since the remaining ketone group in the molecule was unsaturated, it had to be located on C12. In this position it could accept a hydrogen bond from the C8b phenol proton, which appeared as a sharp singlet at δ 12.40. The downfield shift of H11 (δ 2.52 dq, J=3.5, 6.5 Hz) was appropriate for a methine located α to a ketone. The C10 carbinol methine proton (δ 4.49 dq, J=7.0, 3.5 Hz) showed vicinal coupling to H11 and to the C18 methyl group. All heteronuclear correlations, including those from the C19 methyl protons to C10, C11 and C12, were fully consistent with the proposed structure for compound 8.

Other physicochemical and spectral data for compound 8 (FIG. 1) were as follows: $[\alpha]_D$+30° (CHCl$_3$, c 0.5); IR (film) $v_{max}$ 2960, 1706, 1644, 1625, 1442, 1131 cm$^{-1}$; HREIMS obs. m/z 388.1890, calc'd for C$_{22}$H$_{28}$O$_6$, 388.1886; low res. MS m/z 388 (19%), 373 (100%), 345 (3%), 329 (5%), 313 (3%), 287 (3%).

Figure 3A:
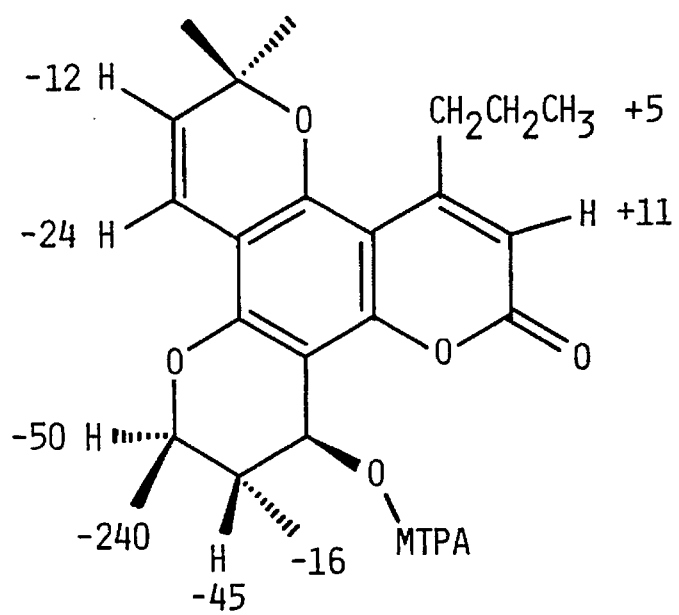
FIG. 3 shows the $^1$H-NMR values ($\Delta\delta=\delta_S-\delta_R$ in Hertz at 500 MHz) for (R)- and (S)-MTPA esters of calanolide A (1) and calanolide B (4) used in the determination of the absolute configuration of calanolides A and B.
Figure 3B:
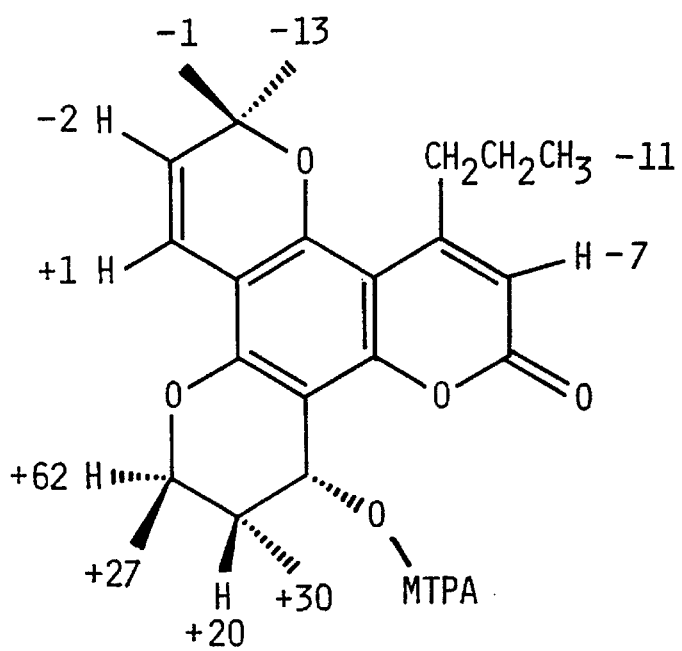
Figure 4A:
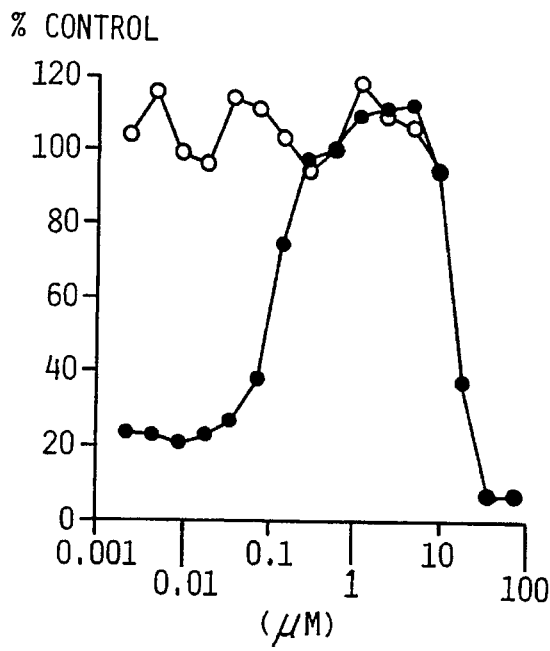
FIGS. 4A, 4B, and 4C show the effects of a range of concentrations of calanolide A upon uninfected CEM-SS cells (o) and upon CEM-SS cells infected with HIV-1 (●), as determined after 6 days in culture.
Figure 4B:
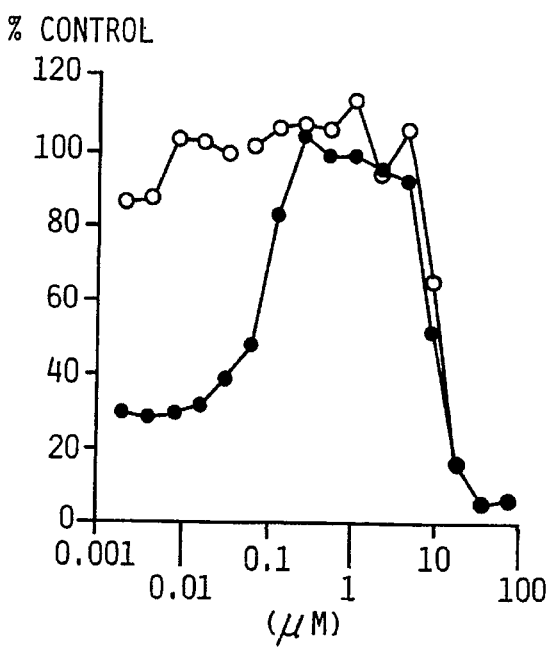
Figure 4C:
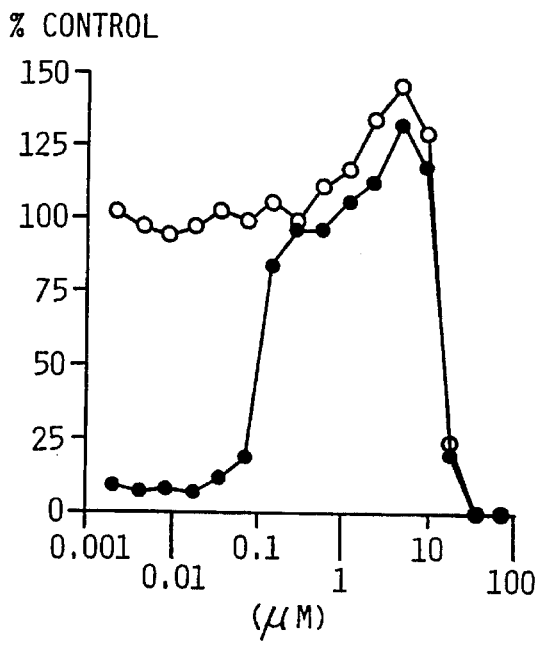
Figure 4D:
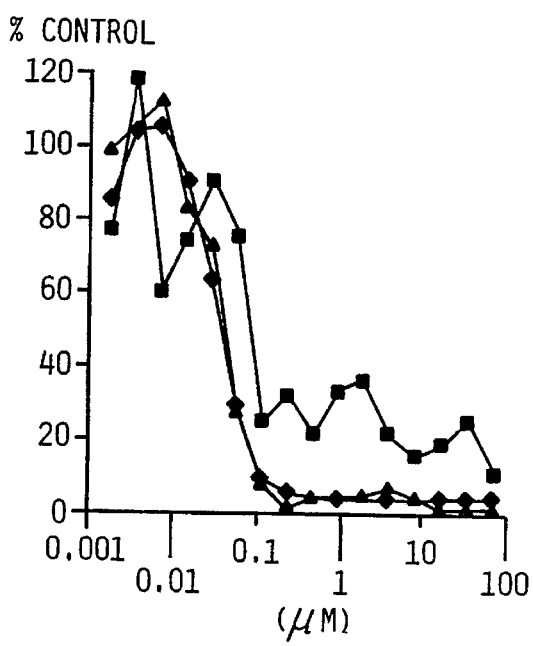
FIG. 4D shows the effects of a range of concentrations of calanolide A upon indices of infectious virus or viral replication; these indices include viral reverse transcriptase (▲), viral core protein p24 (♦) and syncytium-forming units (■).

The absolute stereochemistry of calanolide A (1) and calanolide B (4) was determined by a modified Mosher's method (Ohtani, I., et al., *Tetrahedron Lett.*, 30(24), 3147–3150 (1989); *J. Org. Chem.*, 56, 1296–1298 (1991)). The technique utilized anisotropic shifts induced in the $^1$H NMR spectra of methoxy(trifluoromethyl)-phenylacetic (MTPA) esters of secondary alcohols to define the absolute stereochemistry. Both (+)-(R)- and (−)-(S)-MTPA esters (FIG. 3) of compounds 1 and 4 were prepared.

A solution of (R)-α-methoxy-α-(trifluoromethyl)phenylacetic acid chloride ((R)-MTPA chloride) (2.5 mg in 50 μl of benzene) was added to 3 mg of calanolide A (1) dissolved in 3 ml of dry benzene. A 0.03 mg aliquot of dimethylaminopyridine and 10 μl of triethylamine were added, and the reaction mixture was refluxed. After 3 h, a second 2.5 mg portion of (R)-MTPA chloride was added, and the reaction was refluxed for an additional 21 h. When the mixture was cooled, 10 ml of benzene were added and the organic phase was successively washed with 10% HCl, N NaHCO$_3$, and H$_2$O. The solution was dried over Na$_2$SO$_4$, evaporated to dryness, and then quickly chromatographed on a short plug (1×2 cm) of silica, eluting with mixtures of hexane/EtOAc. A compound which appeared to be an elimination product eluted first with 5% EtOAc, while the desired (S)-MTPA ester eluted with 12% EtOAc. The same procedure was repeated with (S)-MTPA chloride to give the (R)-MTPA ester. The (S)- and (R)-MTPA esters of calanolide B (4) were prepared in an identical fashion, with the exception that, after the second addition of the MTPA chloride, the reaction mixture was refluxed for only an additional 2 h (total time of reflux=5 h). The Δδ values (FIG. 3) from the 500 MHz $^1$H NMR spectra were calculated (Δδ=δ$_S$−δ$_R$). By this method, the absolute configuration of C12 was determined to be 12S in calanolide A (1) and 12R in calanolide B (4). As established earlier, calanolide A (1) [10R, 11R, 12S] and calanolide B (4) [10R, 11R, 12R] were C12 epimers.

Esterification of calanolide A (1) occurred slowly (24 hr reflux for compound 1 vs. 5 hr for compound 4), and, by $^1$H NMR analysis, esterification appeared to cause a change in the conformation of the chromanol ring. The methyls and the ester group flipped from equatorial to axial positions in the MTPA ester of compound 1, as $J_{10-11}$=2.5 Hz (previously 9.0 Hz) and $J_{11-12}$=2.5 Hz (previously 8.0 Hz). In addition, a 4-bond W coupling of 1.5 Hz between H10 and H12 also could be observed. Similar changes in the conformation of the chromanol ring were previously noted for compound 3. The anisotropic shifts induced in the MTPA esters indicated that the bulky MTPA group was sterically repulsed by the coumarin ring lactone. Thus, the plane that divided the molecule's proton resonances into Δδ-positive and Δδ-negative did not cleanly bisect the dihydropyran ring through C12 and O9. In calanolide A (1), the dividing plane seemed to come closer to C6 and, in calanolide B (4), to C8b. Due to the 1,3-diaxial orientation of the C10β-methyl and the C12β-ester group in the MTPA ester of compound 1, the former methyl group was very strongly influenced by the ester ($\Delta\delta=-240$ in comparison to $-16$ measured for the C11α-methyl).

Summaries of the 500 MHz $^1$H-NMR data and the 125 MHz $^{13}$C-NMR data for compounds 1–8 (FIG. 1) are provided in Tables 1 and 2, respectively.

TABLE 1

500 MHz $^1$H NMR Data for Compounds 1–8[a]

| Proton # | 1 | 2 | 3 | 4 | 5 | 6 | 7 | 8 |
|---|---|---|---|---|---|---|---|---|
| 3 | 5.92,t, J = 1.0 Hz | 5.93,t, J = 1.0 Hz | 5.94,t, J = 1.0 Hz | 5.93,t, J = 1.0 Hz | 5.92,t, J = 1.0 Hz | 5.94,t, J = 1.0 Hz | 5.98,t, J = 1.0 Hz | 2.67,dd, J = 6.5, 15.0 Hz 2.81,dd, J = 9.0, 15.0 Hz |
| 4 | | | | | | | | 3.67,br m |
| 7 | 5.52,d, J = 9.5 Hz | 5.52,d, J = 10.0 Hz | 5.50,d, J = 10.0 Hz | 5.51,d, J = 10.0 Hz | 5.51,d, J = 10.0 Hz | 5.56,d, J = 10.5 Hz | 5.61,d, J = 11.0 Hz | 5.45,d, J = 10.0 Hz |
| 8 | 6.60,d, J = 9.5 Hz | 6.61,d, J = 10.0 Hz | 6.61,d, J = 10.0 Hz | 6.61,d, J = 10.0 Hz | 6.60,d, J = 10.0 Hz | 6.83,d, J = 10.5 Hz | 6.78,d, J = 11.0 Hz | 6.58,d, J = 10.0 Hz |
| 10 | 3.90,dq, J-9.0, 6.5 Hz | 4.16,quin, J = 6.5 Hz | 4.26,ddq, J = 1.3, 3.5, 6.5 Hz | 4.24,dq, J = 10.5, 6.5 Hz | 4.27,dq, J = 11.0, 6.0 Hz | 4.32,dq, J = 2.5, 7.0 Hz | 4.69,dq, J = 3.0, 6.5 Hz | 4.49,dq, J = 3.5, 7.0 Hz |
| 11 | 1.91,ddq, J = 9.0, 8.0, 6.5 Hz | 2.09,ddd, J = 6.0, 6.5, 7.5 Hz | 2.23,ddq, J = 3.5, 3.7, 7.5 Hz | 1.73,ddq, J = 10.5, 3.3, 6.5 Hz | 1.69,ddq, J = 11.0, 2.5, 6.0 Hz | 2.22,ddq, J = 2.5, 6.0, 7.0 Hz | 2.61,dq, J = 3.0, 7.0 Hz | 2.52,dq, J = 3.5, 6.5 Hz |
| 12 | 4.70,d, J = 8.0 Hz | 5.97,d, J = 6.0 Hz | 4.31,dd, J = 3.7, 1.3 Hz | 4.95,d, J = 3.3 Hz | 4.54,d, J = 2.5 Hz | 5.06,dd, J = 6.0, 1.5 Hz | | |
| 13,13' | 2.87,m | 2.86,m | 2.80,m 2.92,m | 2.87,m | 2.88,m | 2.88,m 2.79,m | 2.85,m | 1.50,m 1.80,m |
| 14,14' | 1.63,m | 1.63,sext, J = 7.0 Hz | 1.63,m | 1.63,sext, J = 7.0 Hz | 1.64,sext, J = 7.0 Hz | 1.60,sext, J = 7.0 Hz | 1.63,sext, J = 7.0 Hz | 1.14,m(2H) |
| 15 | 1.01,t, J = 7.5 Hz | 1.01,t, J = 7.0 Hz | 1.01,t, J = 7.5 Hz | 1.01,t, J = 7.5 Hz | 1.01,t, J = 7.5 Hz | 0.98,t, J = 7.5 Hz | 1.01,t, J = 7.5 Hz | 0.84,t, J = 7.0 Hz |
| 16 | 1.44,s | 1.46,s | 1.47,s | 1.46,s | 1.46,s | 1.46,s | 1.50,s[b] | 1.41,s |
| 17 | 1.49,s | 1.49,s | 1.45,s | 1.47,s | 1.47,s | 1.46,s | 1.50,s[b] | 1.45,s |
| 18 | 1.44,d, J = 6.5 Hz | 1.43,d, J = 6.5 Hz | 1.45,d, J = 7.0 Hz | 1.41,d, J = 6.0 Hz | 1.38,d, J = 6.5 Hz | 1.41,d, J = 7.0 Hz | 1.42,d, J = 7.0 Hz | 1.35,d, J = 7.0 Hz |
| 19 | 1.13,d, J = 6.5 Hz | 1.05,d, J = 7.5 Hz | 1.00,d, J = 7.5 Hz | 1.12,d, J = 7.0 Hz | 1.13,d, J = 6.5 Hz | 1.06,d, J = 7.5 Hz | 1.14,d, J = 7.0 Hz | 1.12,d, J = 6.5 Hz |
| OR | 3.55,brs (OH) | 2.10,s (OAc) | 3.59,s (OMe) | 2.43,brs (OH) | 3.58,s (OMe) | 3.64,d, J = 1.5 Hz (OH) | | 12.4,s (OH) |

[a]Spectra obtained in CDCl$_3$. Compounds 1, 7 and 8 were assigned by HMQC, HMBC, COSY and difference nOe experiments. Assignments for compounds 2–6 were made by analogy.
[b]Two peaks separated by 0.04 Hz

TABLE 2

125 MHz $^{13}$C NMR Data for Compounds 1–8[a]

| CARBON # | 1 | 2 | 3 | 4 | 5 | 6 | 7 | 8 |
|---|---|---|---|---|---|---|---|---|
| 2 | 160.4 | 160.0 | 160.9 | 160.9 | 160.8 | 160.8 | 160.0 | 178.6 |
| 3 | 110.1 | 110.9 | 110.7 | 110.3 | 110.3 | 111.1 | 111.4 | 38.5 |
| 4 | 158.9 | 157.7 | 158.2 | 158.7 | 158.5 | 158.6 | 158.1 | 30.5 |
| 4a | 104.0 | 101.1[b] | 102.7 | 103.5 | 103.2 | 103.5[b] | 102.7 | 108.9 |
| 4b | 151.1 | 151.7 | 151.6 | 151.4 | 151.4 | 150.6 | 157.6 | 157.3 |
| 6 | 76.6 | 77.8 | 77.6 | 77.7 | 77.6 | 78.8 | 78.9 | 78.2 |
| 7 | 126.9 | 126.8 | 126.6 | 126.7 | 126.6 | 126.9 | 128.2 | 125.6 |
| 8 | 116.5 | 116.4 | 116.6 | 116.5 | 116.6 | 115.7 | 115.0 | 115.6 |
| 8a | 106.3 | 104.1[b] | 104.1 | 106.1[b] | 104.7[b] | 102.9[b] | 104.1 | 102.6 |
| 8b | 153.1 | 152.6 | 151.6 | 153.9 | 153.8 | 152.6 | 160.0 | 160.0[c] |
| 10 | 77.7 | 76.6 | 73.8 | 73.0 | 73.4 | 75.6 | 77.4 | 76.1 |
| 11 | 40.5 | 38.6[c] | 35.1 | 38.66 | 38.6[c] | 35.1 | 45.7 | 44.2 |
| 12 | 67.2 | 67.1 | 77.6 | 61.9 | 70.8 | 65.9 | 192.9 | 201.0 |
| 12a | 106.3 | 106.2[b] | 106.4 | 106.2[b] | 106.0[b] | 109.2[b] | 106.8 | 101.2 |
| 12b | 154.4 | 154.4 | 155.1 | 153.1 | 153.1 | 154.6 | 154.3 | 160.0[c] |
| 13 | 38.7 | 38.1[c] | 38.6 | 38.2[c] | 38.65 | 38.9 | 38.9 | 35.4 |

TABLE 2-continued

125 MHz $^{13}$C NMR Data for Compounds 1–8[a]

| CARBON # | 1 | 2 | 3 | 4 | 5 | 6 | 7 | 8 |
|---|---|---|---|---|---|---|---|---|
| 14 | 23.3 | 23.3 | 23.3 | 23.3 | 23.3 | 23.2 | 23.0 | 20.7 |
| 15 | 14.0 | 14.0 | 14.0 | 14.0 | 14.1 | 14.0 | 13.9 | 14.0 |
| 16 | 27.4 | 27.8 | 27.7 | 27.8 | 27.8 | 28.2 | 28.0 | 28.1 |
| 17 | 28.0 | 28.0 | 27.9 | 27.7 | 27.9 | 28.4 | 28.1 | 28.5 |
| 18 | 18.9 | 19.2 | 19.5 | 18.9 | 19.2 | 16.8 | 15.9 | 16.2 |
| 19 | 15.1 | 15.3 | 17.0 | 12.5 | 13.3 | 7.2 | 9.0 | 9.3 |
|  |  | 170.7[d] | 57.6[e] |  | 59.4[e] |  |  |  |
|  |  | 21.2[d] |  |  |  |  |  |  |

[a]Spectra recorded in CDCl$_3$ and attached protons determined by the DEPT pulse sequence.
[b,c]Resonances within a column may be interchangeable.
[d]Acetyl resonances.
[e]Methoxy resonances.
[f]In CD$_3$OD these signals appeared as doubled peaks at δ 161.20, 161.16 and δ 161.10, 161.03.

Example 4

This example illustrates the antiviral activity of calanolides and related compounds from *Calophyllum lanigerum* Miq. var. austrocoriaceum (T. C. Whitmore) P. F. Stevens. Pure compounds were initially evaluated for antiviral activity using an XTT-tetrazolium anti-HIV primary screening assay described previously (Boyd, M. R., in *AIDS Etiology, Diagnosis, Treatment and Prevention* (DeVita V. T., Jr., Hellman S., Rosenberg S. A., eds.), pp 305–319 (Philadelphia: Lippincott, 1988); Gustafson, K. R., et al., *J. Med. Chem.*, 35, 1978–1986 (1992); Weislow, O. S., et al., *J. Natl. Cancer Inst.*, 81, 577–586 (1989); Gulakowski, R. J., et al., *J. Virol. Methods*, 33, 87–100 (1991)). The CEM-SS human lymphocytic target cell line used in all assays was maintained in RPMI 1640 medium (Gibco, Grand Island, N.Y.), without phenol red, and was supplemented with 5% fetal bovine serum, 2 mM L-glutamine and 50 µg/ml gentamicin (complete medium). Exponentially-growing cells were pelleted and resuspended at a concentration of 2.0×10$^5$ cells/ml in complete medium. The Haitian variant of HIV, HTLV-III$_{RF}$ (3.54×10$^6$ SFU/ml), was used throughout. Frozen virus stock solutions were thawed immediately before use and resuspended in complete medium to yield 1.2×12$^5$ SFU/ml. The appropriate amounts of the pure compounds for anti-HIV evaluations were dissolved in 100% dimethylsulfoxide (DMSO), then diluted in complete medium to the desired initial concentration (and with the final DMSO content not exceeding 1%). All serial drug dilutions, reagent additions, and plate-to-plate transfers were carried out with an automated Biomek 1000 Workstation (Beckman Instruments, Palo Alto, Calif.).

Over a broad concentration range (<0.1–>10 µM), calanolide A (1) provided complete protection against the cytopathic effects of HIV-1 infection in the primary screening assay and essentially halted HIV-1 reproduction in human T-lymphoblastic (CEM-SS) cells. Calanolide B (4), the C12 epimer of compound 1, also provided complete inhibition of HIV-1 in this assay, giving an EC$_{50}$=0.4 µM and an IC$_{50}$=15.0 µM. The ester derivative, 12-acetoxycalanolide A (2) also was active against HIV-1, albeit somewhat less potent (EC$_{50}$=2.7 µM, IC$_{50}$=13 µM). Compound 6 showed weak but detectable anti-HIV activity, as did the 12-methoxycalanolide S (5); however, the antiviral activity of the corresponding 12-methoxycalanolide A (3) was not detectable in the primary screen. Compounds 7 and 8 were inactive in the primary screening assay, indicating the requirement for a fully reduced oxygen functionality, or derivative substitutent thereof, at C-12, and the further requirement for the intact, characteristic central carbon skeleton shared by compounds 1–6.

For a further demonstration of the anti-HIV activity of pure compounds, a battery of interrelated assays was performed on individual wells of 96-well microtiter plates as described in detail elsewhere (Gulakowski, R. J. et al., *J. Virol. Methods*, 33, 87–100 (1991)). Briefly, the procedure was as follows. Uninfected CEM-SS cells were plated at a density of 1×10$^4$ cells in 50 µl of complete medium. Diluted HIV-1 virus was then added to appropriate wells in a volume of 50 µl to yield a multiplicity of infection of 0.6. Appropriate cell, virus and drug controls were incorporated in each experiment; the final volume in each microtiter well was 200 µl. Quadruplicate wells were used for virus-infected cells, and duplicate wells were used for uninfected cells. Plates were incubated at 37° C. in an atmosphere containing 5% CO$_2$ for 6 days. Subsequently, aliquots of cell-free supernatant were removed from each well using the Biomek, and analyzed for reverse transcriptase activity, p24 antigen production and synthesis of infectious virions as described (Gulakowski, R. J., et al., *J. Virol. Methods*, 33, 87–100 (1991)). Cellular growth or viability then was estimated on the remaining contents of each well using the XTT (Weislow, O. S., et al., *J. Natl. Cancer Inst.*, 81, 577–586 (1989)), BCECF (Rink, T. L., et al., *J. Cell. Biol.*, 95, 189–196 (1982)) and DAPI (McCaffrey, T. A., et al., *In Vitro Cell Develop. Biol.*, 24, 247–252 (1988)) assays as described (Gulakowski, R. J., et al., *J. Virol. Methods*, 33, 87–100 (1991)). To facilitate graphical displays and comparisons of data, the individual experimental assay results (of at least quadruplicate determinations of each) were averaged, and the mean values were used to calculate percentages in reference to the appropriate controls. Standard errors of the mean values used in these calculations typically averaged less than 10% of the respective mean values.

As illustrated in FIGS. 4A–D, calanolide A was capable of complete inhibition of the cytopathic effects of HIV-1 upon CEM-SS human lymphoblastoid target cells in vitro (EC$_{50}$~ 0.1 µM); direct cytotoxicity of the compound upon the target cells was apparent only at 100-fold greater concentrations (IC$_{50}$~ 13 µM; in vitro "therapeutic index" ≧130). Calanolide A also strikingly inhibited the production of RT, p24, and SFU in HIV-1-infected CEM-SS within these same inhibitory effective concentrations, indicating a cessation of viral replication. Similar results (data not shown) as those depicted for calanolide A in FIGS. 4A–D were also obtained with calanolide B, with a noncytotoxic concentration of the latter completely inhibiting HIV-replication and affording complete protection against HIV cytopathicity.

Example 5

This example illustrates antiviral calanolide derivatives and related antiviral compounds. One skilled in the art will appreciate that other antiviral calanolides or antiviral derivatives thereof, in addition to the calanolides and derivatives of Example 3, may be isolated from natural sources and/or be synthesized chemically. Antiviral calanolides or antiviral derivatives thereof can comprise two distinct series, as illustrated more generally in FIG. 5. For example, calanolide A (1) from Example 3 is of series 1, wherein $R^1$ is $CH_2CH_2CH_3$, $R^2$ is ◄ OH, $R^4$ is ⋯ $CH_3$, and $R^5$ is ◄ $CH_3$. Calanolide B (4) from Example 3 is of series 1, wherein $R^1$ is $CH_2CH_2CH_3$, $R^2$ is ⋯ OH, $R^4$ is ⋯ $CH_3$, and $R^5$ is ◄ $CH_3$. Compound 2 from Example 3 is of series 1, wherein $R^1$ is $CH_2CH_2CH_3$, $R^2$ is ◄ $O_2CR^3$, $R^3$ is —$CH_3$, $R^4$ is ⋯ $CH_3$, and $R^5$ is ◄ $CH_3$. Compound 3 from Example 3 is of series 1 wherein $R^1$ is $CH_2CH_2CH_3$, $R^2$ is ◄ $OR^3$, $R^3$ is —$CH_3$, $R^4$ is ⋯ $CH_3$, and $R^5$ is ◄ $CH_3$. Compound 5 from Example 3 is of series 1, wherein $R^1$ is $CH_2CH_2CH_3$, $R^2$ is ⋯ $OR^3$, $R^3$ is —$CH_3$, $R^4$ is ⋯ $CH_3$, and $R^5$ is ◄ $CH_3$. Compound 6 from Example 3 is of series 1, wherein $R^1$ is $CH_2CH_2CH_3$, $R^2$ is ◄ OH, and $R^4$ and $R^5$ are each ◄ $CH_3$. The previously known, naturally-occurring compound (Stout, G. H., and Stevens, K. L., *J. Org. Chem.*, 29, 3604–3609 (1964)) costatolide (compound 9 of FIG. 2) is an example of series 1, wherein $R^1$ is $CH_2CH_2CH_3$, $R^2$ is ◄ OH, $R^4$ is ◄ $CH_3$, and $R^5$ is ⋯ $CH_3$. Compound 7 from Example 3 illustrates a related natural product from *Calophyllum lanigerum* which has the same carbon skeleton that characterizes members of series 1, wherein $R^1$ is $CH_2CH_2CH_3$ and $R^4$ and $R^5$ are each ◄ $CH_3$.

Whereas the above examples provide the essential precedents for the characteristic structural (stereochemical and substituent) features about C-10, C-11, and C-12 relative to the antiviral calanolides and antiviral derivatives thereof of FIG. 5, there are also precedents for variations at $R^1$ provided by related naturally occurring compounds having variations at C-4. For example, compounds, which have the same central carbon skeleton that characterize the antiviral calanolides and antiviral derivatives thereof of FIG. 5, have been isolated that have $CH_3$ or aryl substituents at C-4 (Dharmaratne, H. R. W., et al., *Phytochemistry*, 24, 1553–1556 (1985); Gunasekera, S. P., et al., *J. Chem. Soc. Perkin I*, 1505–1511 (1977)), but differ in the stereochemistry and/or substituents at C-10, C-11, and C-12 that characterize the calanolides. For example, the previously known (Gunasekera, S. P., et al., *J. Chem. Soc. Perkin I*, 1505–1511 (1977)), naturally occurring compound soulattrolide (compound 14 of FIG. 2) is an example of a series 1 compound, wherein $R^1$ is $C_6H_5$, $R^2$ is ◄ OH, $R^4$ is ◄ $CH_3$, and $R^5$ is ⋯ $CH_3$.

As a more specific illustration, the isolation and purification of costatolide (9) and soulattrolide (14) from latex of *Calophyllum teysmannii* var. inophylloide is provided in Example 8 below. The previously unknown antiviral activity of these two compounds is shown in Example 10 and Table 6 below.

Whereas the above examples provide precedents for the isolation of naturally occurring antiviral calanolides and antiviral derivatives thereof, and of other natural products that show the essential structural features of antiviral calanolides and derivatives thereof of series 1, one skilled in the art also will appreciate that, using standard organic chemical methodology, a number of structural modifications can be made for purposes of preparing antiviral calanolides or antiviral derivatives thereof. For example, antiviral calanolides and antiviral derivatives of series 2 can be made from calanolides or derivatives thereof of series 1. More specifically, an antiviral member of series 1 may be converted to the corresponding member of series 2, wherein C7 and C8 of the latter are fully saturated. 7,8-dihydro calanolide A of series 2 can be made from calanolide A of series 1 by platinum oxide-catalyzed hydrogenation of the 7,8 olefinic linkage.

Example 9 below more specifically illustrates the conversion of series 1 compounds (calanolide A, calanolide B, costatolide, and soulattrolide) to series 2 compounds (7,8-dihydrocalanolide A, 7,8-dihydrocalanolide B, 7,8-dihydrocostatolide, and 7,8-dihydrosoulattrolide, respectively).

As a further example, an antiviral member of either series 1 or 2, wherein $R^2$ is ◄ OH or ⋯ OH can be converted to the corresponding C-12 ester or sulfonate ester wherein $R^2$ is ◄ $O_2CR^3$, ⋯ $O_2CR^3$, ◄ $O_3SR^3$, or ⋯ $O_3SR^3$, by reaction with the corresponding acid halide, X—$OCR^3$, or X—$O_2SR^3$, where X=Cl, Br, or I, and $R^3$ is $C_1$–$C_6$ alkyl or aryl, or, alternatively, by reaction directly with the corresponding acids, $HO_2CR^3$, or $HO_3SR^3$, wherein $R^3$ is $C_1$–$C_6$ alkyl or aryl, and dicyclohexylcarbodiimide in anhydrous pyridine or triethylamine. Vice versa, a C-12 ester of either series 1 or 2, wherein $R^2$ is ◄ $O_2CR^3$, ⋯ $O_2CR^3$, ◄ $O_3SR^3$ or ⋯ $O_3SR^3$, and $R^3$ is $C_1$–$C_6$ alkyl or aryl, may be hydrolyzed chemically or enzymatically to the respective parent calanolide compound, wherein $R^2$ is ◄ OH or ⋯ OH. It is further noted that calanolide derivatives esterified at C-12, which are susceptible to plasma- or tissue-esterase mediated deesterification, can serve as prodrugs in vivo for antiviral calanolides, wherein the C-12 substituent is ◄ OH or ⋯ OH.

Example 6

This example sets forth the taxonomic characteristics of *Calophyllum teysmannii* var. inophylloide (Soejarto et al. 7853, 7854, 7899, 7900, 7901, 7902) used in Examples 7 and 8. Of the five trees with dbh>30 cm, tree 7854 grows on a ridge, while 7899–7902 are found along gentle slopes, towards streams found at lower sides of these slopes, in a deep kerangas forest at Sampedi Forest Reserve, which has been selectively logged. These 5 trees are situated along a more-or-less straight line, each tree separated from the other by a distance of between 40 and 75 m; the distance between trees 7854 and 7902 (at the opposite ends of the straight line) is about 300 m. Further search indicated that within this 0.3 hectare of this forest, only those 5 large trees of *Calophyllum teysmannii* var. inophylloide were present. Based on this observation, it was estimated that approximately 15 large (dbh>30 cm) trees might be expected to be found in a one-hectare forest in this locality. However, many more small trees of this species (saplings and seedlings) were found.

These five trees are characterized taxonomically as follows: tree 12–25 m tall, dbh 30–60 cm, trunk at base with low spurs, bark gray-brown to gray-black, roughly fissured, cracked, and scaling off, slash light pinkish red to pinkish brown, latex clear-yellow, seeping out as tiny droplets or en masse and collecting on the cut surface of the bark, sticky;

twigs slightly flattened-to-angled, covered with blackish brown pubescence, terminal buds small, somewhat conical and flattened, 1 cm long, covered by similar pubescence as the twig; leaves strongly coriaceous, dark olive-brown above, paler beneath, narrowly obovate to elliptic-obovate-to-oblong, 10–18 cm long, 3–6 cm wide, apex rounded, base cuneate to rounded-cuneate, margins entire sharply recurved, veins 14–16 per 5 mm, petiole 1.5–2 cm long, canaliculate. All trees were sterile at the time of collection. The characteristic features of *Calophyllum teysmannii* var. inophylloide as compared to *Calophyllum lanigerum* var. austrocoriaceum are summarized in Table 3. According to Stevens, P. F., *J. Arnold Arbor.*, 61, 356–361, 431–443 (1980), sterile specimens of *C. teysmannii* var. inophylloide are distinguished from *C. lanigerum* var. austrocoriaceum by the larger tree size, the dark brown to blackish, rough and coarsely fissured and cracked trunkbark (vs. the lighter colored, smoothish and lenticellate bark of *C. langerium* var. austrocoriaceum), the smaller and less plump terminal buds, the normally less elongate leaves which are more strongly coriaceous in texture, and the recurved leaf margins.

Slashing method: clean slashes (cuts) of varying sizes, 3–25 cm long by 1.5–3 cm wide, were made using a large cutting tool (a machete or "parang"), taking care not to cut the cambium layer. From 4 to 9 slashes per tree at breast high were made. Direction of slashes ranges from horizontal (perpendicular to the tree axis) to a slant of 45° angle. After enough latex has accumulated on the slashed surfaces, this is scraped carefully using a pocket knife.

Scraping method: a pocket knife is held and traced along the contour of the slash/cut to gather the latex. (a) One scraping operation was made from all the slashes on every tree in late morning of Jan. 7, 1993; the total latex sample from all slashes on one tree was placed in a small plastic bag. (b) A second scraping was made on all slashes of every tree in the late afternoon of Jan. 7, 1993; the total latex sample from a number of slashes on one tree was placed in a small plastic bag, separate from the morning scraping. (c) A third scraping was made on all slashes of every tree in the morning of Jan. 8, 1993; the total latex from a number of slashes on one tree was placed in a small plastic bag, separate from those made on Jan. 7, 1993. (d) A fourth

TABLE 3

Distinguishing features between *Calophyllum teysmannii* var. *inophylloide* and *Calophyllum lanigerum* var. *austrocoriaceum*

| | | |
|---|---|---|
| Tree | to 40 m tall, dbh to 95 cm | to 21 m tall, dbh to 48 cm |
| Bark | gray-black, roughly fissured and cracked | brownish yellow to dark brown, smoothish and lenticellate, either irregularly arranged in a ring or in longitudinal rows |
| Trunkbase | with spurs/small buttresses at base | no spur or buttresse |
| Leaf blade | elongate ovate to elliptic to oblong 7–17 cm long by 3–5 cm wide, strongly coriaceous margins recurved | obovate to narrowly ovate to oblong, 4–20 cm long by 3–8 cm wide, coriaceous margins not recurved |
| Lateral veins | 6–21 per 5 mm | 6–15 per mm |
| Terminal bud | small, 0.2–1 cm long | large and plump, 1.5–3 cm long |

Example 7

This example illustrates the collection of latex (resinous exudate) from the *Calophyllum teysmannii* var. inophylloide trees of Example 6 (Soejarto et al. 7853, 7854, 7899, 7900, 7901, 7902). On the trunkbark at breast-high of tree 7854, two old wounds (slashes) made on Jul. 19, 1992, had healed by the visit of Jan. 7, 1993. On these old wounds, latex crusts that had dried up from the July 1992 cuts remained. These latex crusts were of opaque, light yellowish color. These were collected by scraping the dried crusts with a pocket knife and placing them in a small polyethylene (plastic) bag. In addition to these old wounds, new slashes were made, from which a fresh latex sample was collected and placed in a separate plastic bag. All latex samples were numbered accordingly.

Slashes were also made on trees 7899–7902, and latex samples scraped from the cut surfaces, where enough quantity would collect within 5–20 minutes after a slash was made. Since the latex is scanty and is not free-flowing, the term "tapping" is not appropriate for collecting latex samples of Calophyllum species. The term "scraping," such as by using a pocket knife, is more appropriate.

scraping was made on all slashes of every tree on the week of Jan. 11, 1993; the total latex from a number of slashes on one tree was placed in a small plastic bag, separate from those made previously.

It was noticed that all latex samples changed in appearance (color) from clear-yellow (upon exudating on the cut surface) to opaque-yellow, following scraping and handling in the plastic bag. When dry (in the bag), it became "crumbly" to more-or-less "sandy" in texture. One day after collection, latex samples in the plastic bag emitted a rather strong, characteristic odor, which is not unpleasant.

These samples were kept in a dry place at all times and were packed into several larger plastic bags. These bags were shipped by air to the U.S. as carry-on luggage, without any special treatment or handling, and arrived on Jan. 15, 1993 in good condition; each bag continued to emit the same characteristic odor. A summary of latex yields from the five trees is presented in Table 4.

TABLE 4

Trunkbark-latex yield of *Calophyllum teysmannii* var. *inophylloide*

| Collector's # (NCI Barcode) | Tree DBH | # of Slashes | Jan 7/am | Jan 7/pm | Jan 8/am | Wk Jan 11 | Tot. Yield |
|---|---|---|---|---|---|---|---|
| Soejarto et al. 7853 (U44Z-6117-K) | 16 cm | 7(3–6 cm × 1½–2 cm) | | | (1.5 g) | | (1.5 g) |
| Soejarto et al. 7854 (U44Z-6118-L) | 37 cm | 4(8–20 cm × 1½–3 cm) | 2.5 g | 2.4 g | 3.8 g | 10.0 g | 18.7 g |
| Soejarto et al. 7899 (U44Z-6996-P) | 57 cm | 9(6–15 cm × 1–4 cm) | 1.1 g | 3.4 g | 5.0 g | 10.0 g | 19.5 g |
| Soejarto et al. 7900 (U44Z-6997-Q) | 32 cm | 9(8–13 cm × 1–3 cm) | 1.1 g | 2.0 g | 4.4 g | 8.0 g | 15.5 g |
| Soejarto et al. 7901 (U44Z-6998-R) | 55 cm | 7(5–15 cm × 2–6 cm) | 0.5 g | 2.1 g | 7.7 g | 7.0 g | 17.3 g |
| Soejarto et al. 7902 (U44Z-6999-S) | 45 cm | 9(8–25 cm × 2–5 cm) | 2.6 g | 9.2 g | 2.0 g | 8.5 g | 22.3 g |
| Total trunkbark-latex yield from 5 trees with DBH >30 cm in 4 scrapings | | | | | | | 93.3 g |

Example 8

This example sets forth the isolation of costatolide (compound 9 of FIG. 2) and soulattrolide (compound 14 of FIG. 2) from the latex of Example 7. Neither of these previously known compounds were known to occur in the latex of *Calophyllum teysmannii* var. inophylloide nor were they known to have antiviral activity.

A crude *Calophyllum TEYSMANNII* var. inophylloide latex sample (30 g) was triturated 3 times with 250 ml of CHCl-McOH (1:1). The solution was filtered and evaporated to give 19.9 g of extract. In a typical isolation, 100 mg of resin extract was separated by $SiO_2$ HPLC (41.1×300 mm, Dynamax column) eluted with 75 ml/min hexane/EtOAc (7:3), to give 20 mg of costatolide (retention time= 8.5 min; $[\alpha]_D=-19.7$ ($CHCl_3$, c 1.1); EIMS m/z 370, appropriate for $C_{22}H_{26}O_5$; $^1$H MNR, see Table 5 in Example 9 below), and 13 mg of soulattrolide (retention time=9.6 min; $[\alpha]_D=-25.0$ ($CHCl_3$, c 0.9), EIMS m/z 404, appropriate for $C_{25}H_{24}O_5$; $^1$H NMR, see Table 5 in Example 9 below).

Example 9

Figure 6A:
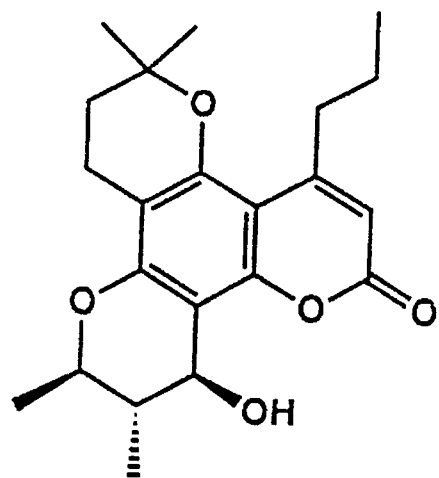
FIGS. 6, A–D, shows examples of antiviral 7,8-dihydrocalanolides and related antiviral 7,8-dihydro compounds.
Figure 6B:
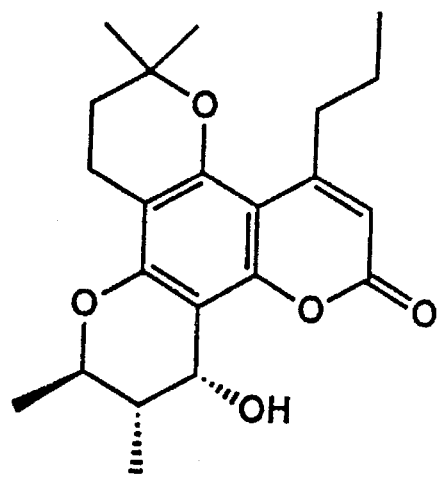
Figure 6C:
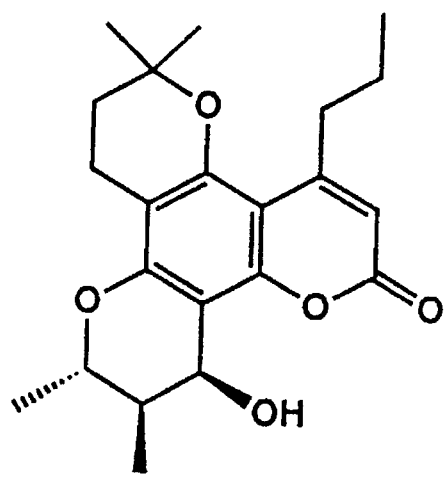
Figure 6D:
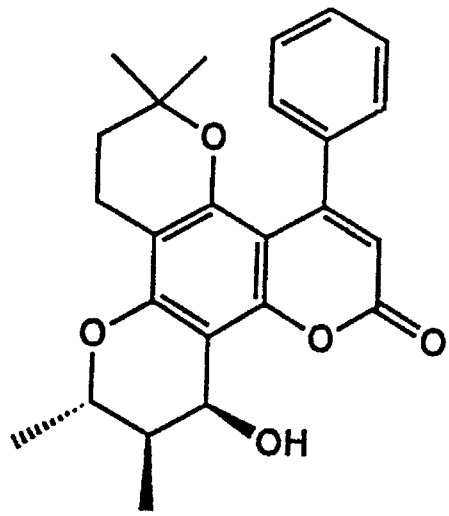
Figure 7A:
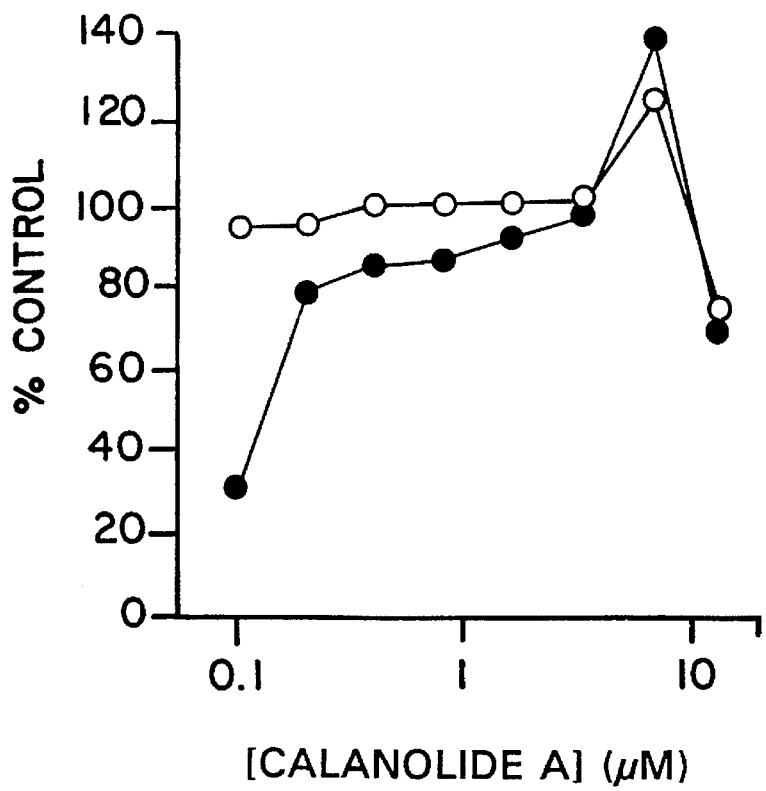
Figure 7B:
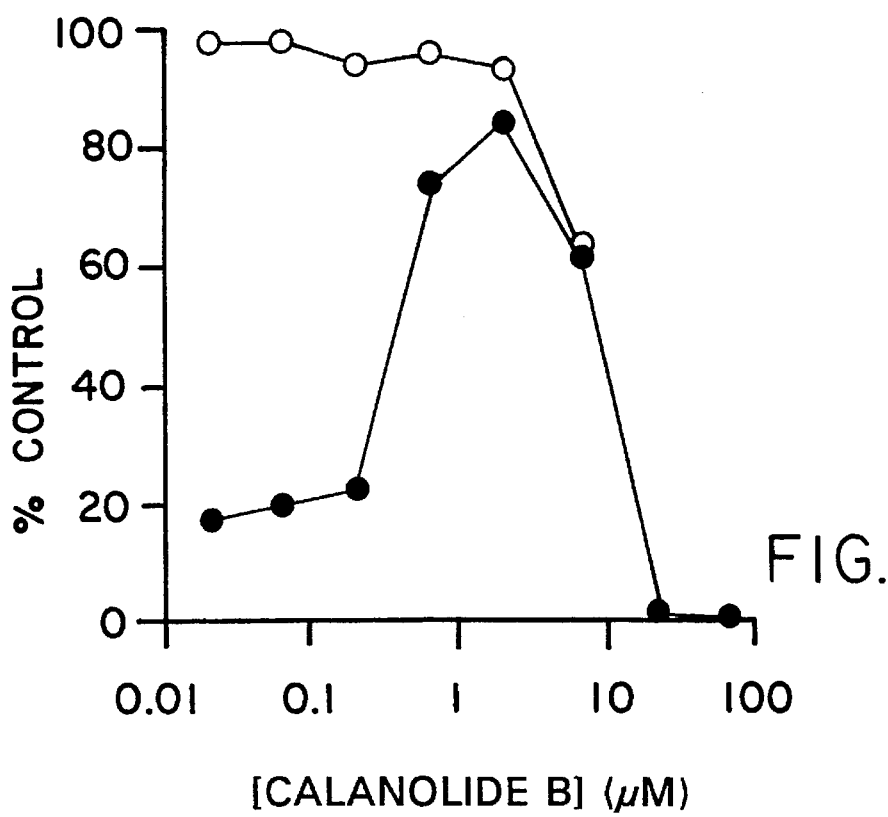
Figure 7C:
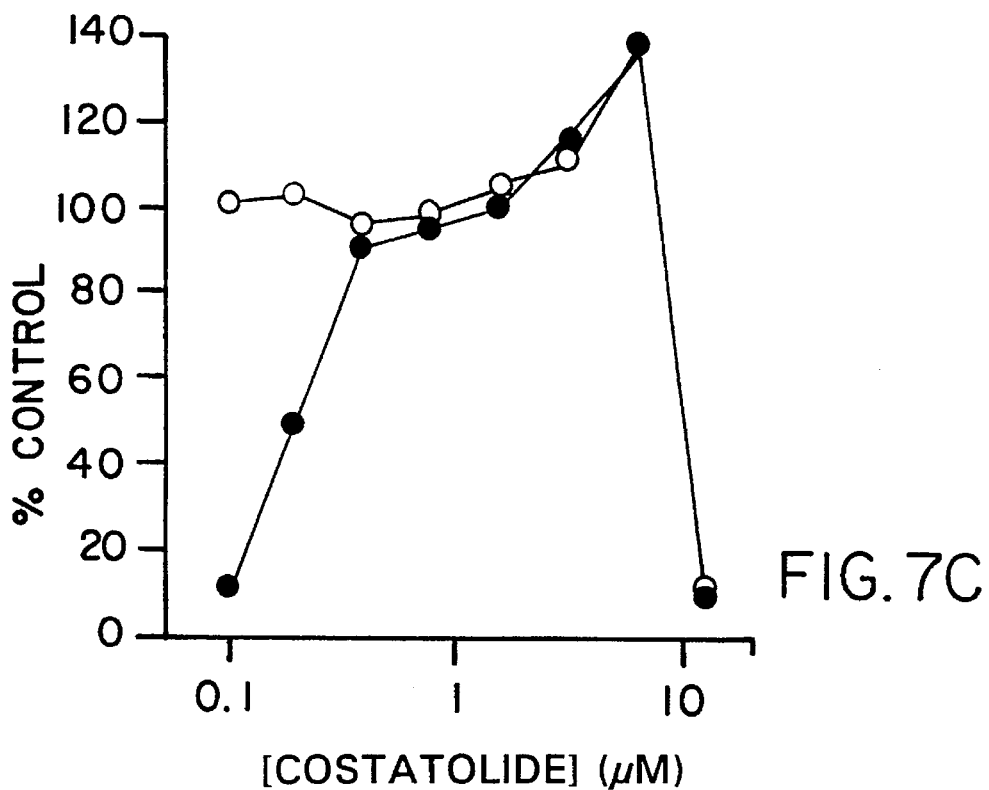
Figure 7D:
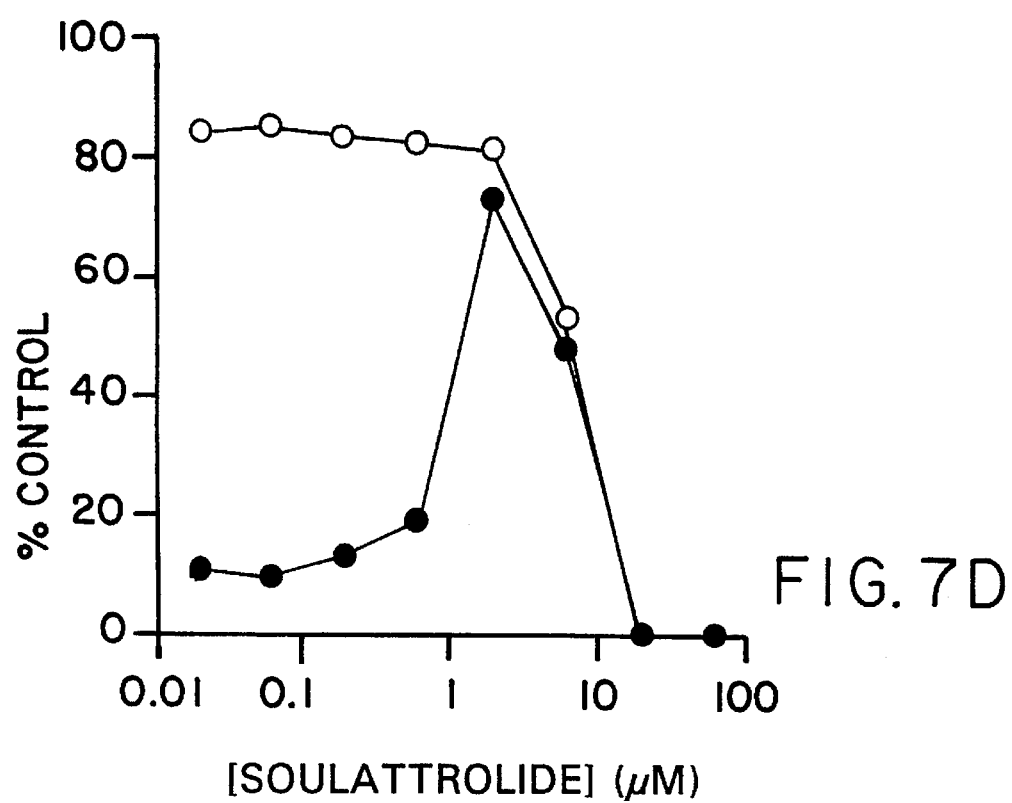
Figure 7E:
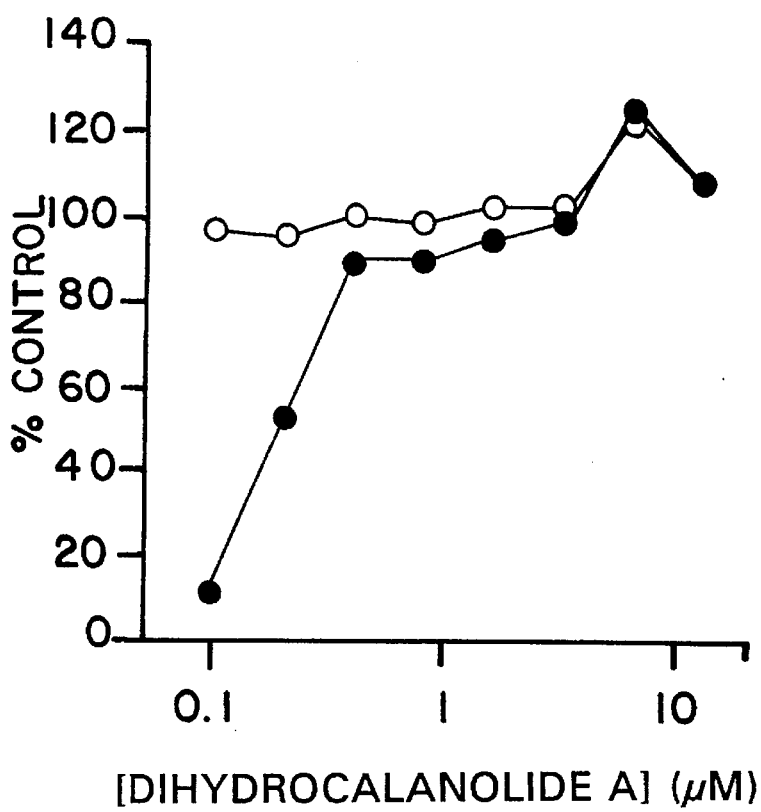
Figure 7F:
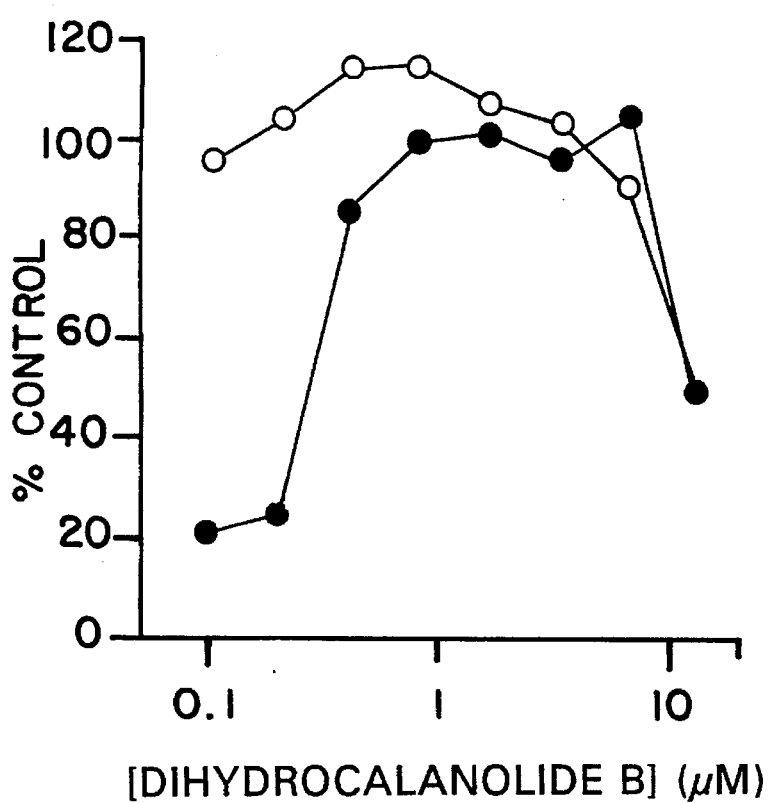
Figure 7G:
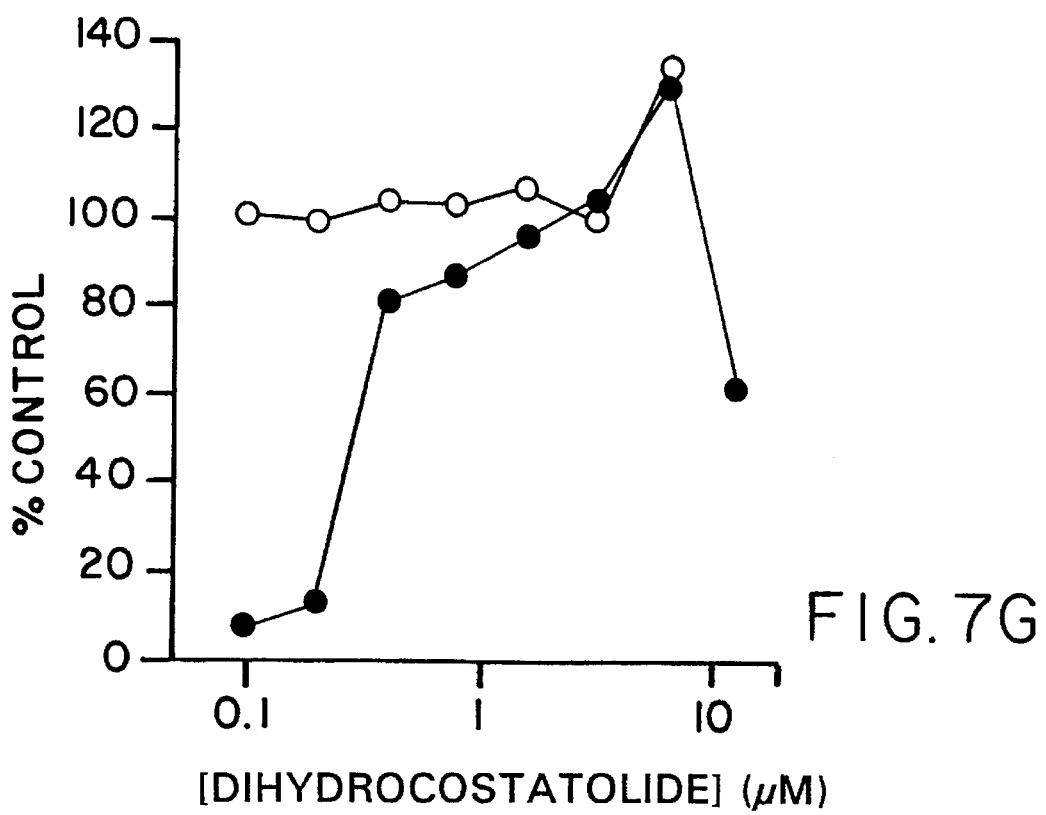
Figure 7H:
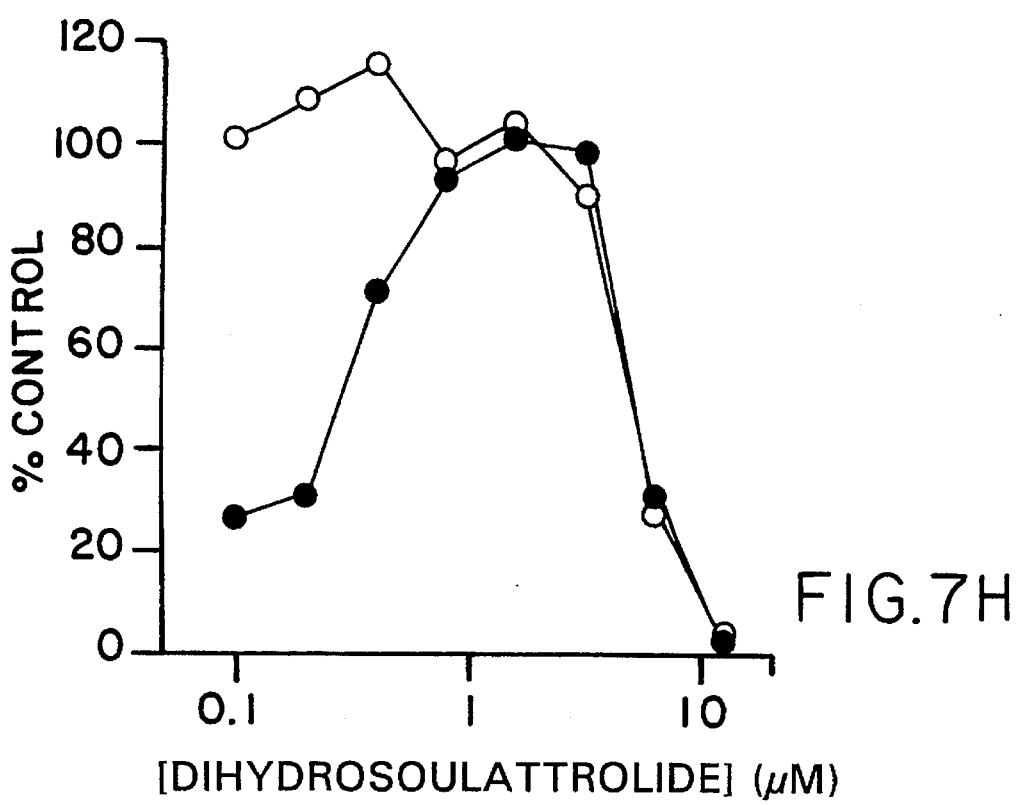

This example illustrates the preparation of antiviral 7,8-dihydro compounds (FIG. 6) of series 2, specifically 7,8-dihydrocalanolide A (FIG. 6A), 7,8-dihydrocalanolide B (FIG. 6B), 7,8-dihydrocostatolide (FIG. 6), and 7,8-dihydrosoulattrolide (FIG. 6D) from the corresponding 7,8-unsaturated compounds of series 1. Of these six compounds, only one structure (7,8-dihydrocostatolide (FIG. 6C); Stout, G. H., et al., *J. Org. Chem.*, 29, 3604–3609 (1964)) had been previously reported, however none of the six were known heretofore to have antiviral activity. The 7,8-dihydro compounds were made by catalytic hydrogenation of the selected appropriate 7,8-unsaturated precursors. In a typical procedure, 10 mg of calanolide A was stirred with 2.5 mg $PtO_2$ (Aldrich) in 4 ml MeOH under an atmosphere of $H_2$ (a balloon filled with $H_2$ was attached to the reaction vessel to provide a slightly positive pressure of $H_2$) for 30 min. The mixture was filtered, and the solvent removed in vacuo to provide a light yellow oil which was purified by $SiO_2$ HPLC (21.1×300 mm, Dynamax column) eluted with 25 ml/min hexane/EtOAc (7:3) to give 9.0 mg of 7,8-dihydrocalanolide A (EIMS m/z 372, appropriate for $C_{22}H_{28}O_5$; $^1$H NMR, see Table 5). In an exactly analogous fashion, 6 mg of calanolide B with 3 mg $PtO_2$ in 4 ml MeOH was converted to 3.6 mg of 7,8-dihydrocalanolide B (EIMS m/z 372, appropriate for $C_{22}H_{28}O_5$; $^1$H NMR, see Table 5); 100 mg of costatolide with 15 mg $PtO_2$ in 20 ml MeOH was converted to 89.9 mg 7,8-dihydrocostatolide (EIMS m/z 372, appropriate for $C_{22}H_{28}O_5$; $^1$H NMR, see Table 5); and 12 mg of soulattrolide with 3 mg $PtO_2$ in 4 ml MeOH was converted to 8.9 mg 7,8-dihydrosoulattrolide (EIMS m/z 406, appropriate for $C_{25}H_{26}O_5$; $^1$H NMR, see Table 5).

TABLE 5

500 MHz NMR Data for Costatolide, Soulattrolide, 7,8-dihydrocalanolide A, 7,8-dihydrocalanolide B, 7,8-dihydrocostatolide, and 7,8-dihydrosoulattrolide

| Proton # | Costatolide | Soulattrolide | 7,8-Dihydrocalanolide A | 7,8-Dihydrocalanolide B | 7,8-Dihydrocostatolide | 7,8-Dihydrosoulattrolide |
|---|---|---|---|---|---|---|
| 3 | 5.93 t J = 1.0 Hz | 5.94 s | 5.90 s | 5.90 s | 5.90 s | 5.92 s |
| 7 | 5.51 d J = 10.0 Hz | 5.34 d J = 9.8 Hz | 1.75 (2H) m | 1.76 (2H) t J = 6.8 Hz | 1.76 (2H) t J = 6.8 Hz | 1.55 (2H) t J = 6.8 |
| 8 | 6.61 d | 6.51 d | 2.61 (2H) m | 2.61 (2H) m | 2.61 (2H) m | 2.53 (2H) m |

TABLE 5-continued

500 MHz NMR Data for Costatolide, Soulattrolide,
7,8-dihydrocalanolide A, 7,8-dihydrocalanolide B, 7,8-dihydrocostatolide, and 7,8-dihydrosoulattrolide

| Proton # | Costatolide | Soulattrolide | 7,8-Dihydrocalanolide A | 7,8-Dihydrocalanolide B | 7,8-Dihydrocostatolide | 7,8-Dihydrosoulattrolide |
|---|---|---|---|---|---|---|
|    | J = 10.0 Hz | J = 9.8 Hz | | | | |
| 10 | 4.24 dq<br>J = 10.5; 6.5 Hz | 4.26 dq<br>J = 10.7; 6.4 Hz | 3.89 dq<br>J = 8.8; 6.4 Hz | 4.22 dq<br>J = 10.7; 6.3 Hz | 4.22 dq<br>J = 10.7; 6.3 Hz | 4.25 dq<br>J = 10.7; 6.4 Hz |
| 11 | 1.73 ddq<br>J = 10.5; 3.3; 6.5 Hz | 1.76 m | 1.88 m | 1.72 m | 1.72 m | 1.75 m |
| 12 | 4.95 d<br>J = 3.3 Hz | 5.02 d<br>J = 3.4 Hz | 4.71 d<br>J = 7.8 Hz | 4.97 d<br>J = 2.9 Hz | 4.97 d<br>J = 2.9 Hz | 5.04 d<br>J = 2.9 |
| 13 | 2.87 m | | 2.83 m; 2.90 m | 2.84 m; 2.89 m | 2.84 m; 2.89 m | |
| 14 | 1.63 sext<br>J = 7.0 Hz | 7.22 (2H) m | 1.60 m | 1.60 sext<br>J = 7.3 Hz | 1.60 sext<br>J = 7.3 Hz | 7.19 (2H) m |
| 15 | 1.01 t<br>J = 7.5 Hz | 7.35 (3H) m | 0.99 t<br>J = 7.4 | 0.99 t<br>J = 7.3 | 0.99 t<br>J = 7.3 | 7.33 (3H) m |
| 16 | 1.46 s | 0.91 s | 1.33 s | 1.35 s | 1.35 s | 0.80 s |
| 17 | 1.47 s | 0.91 s | 1.37 s | 1.35 s | 1.35 s | 0.81 s |
| 18 | 1.41 d<br>J = 6.0 | 1.14 d<br>J = 6.3 Hz | 1.43 d<br>J = 6.4 | 1.40 d<br>J = 5.9 | 1.35 s<br>J = 5.9 | 1.41 d<br>J = 6.4 Hz |
| 19 | 1.12 d<br>J = 7.0 Hz | 1.14 d<br>J = 6.8 | 1.12 d<br>J = 6.8 | 1.12 d<br>J = 7.3 | 1.12 d<br>J = 7.3 Hz | 1.14 d<br>J = 6.8 Hz |

Example 10

This example further illustrates the antiviral activities of the calanolides, related compounds, and derivatives thereof. More specifically, FIG. 7 shows comparative anti-HIV profiles of calanolide A (FIG. 7A), calanolide B (FIG. 7B), costatolide (FIG. 7C), soulattrolide (FIG. 7D), and the four corresponding 7,8-dihydro reduction products (FIG. 7E–H). The profiles were obtained using the XTT anti-HIV-1 assay (described above in Example 4) on all eight compounds tested side-by-side in the same week. In this initial comparison, clearly all eight compounds had strong anti-HIV activity, indeed capable of completely protecting the CEM-SS target cells from the killing effects of HIV-1. However, there did appear to be some modest differences in antiviral potencies (e.g., $EC_{50'\!s}$) and/or direct cytotoxicities (e.g., $IC_{50'\!s}$) to the target cells.

More detailed, quantitative comparison of four of the above compounds was obtained by quadruplicate tests of each compound using two different anti-HIV assay methods, the XTT-based assay as well as the BCECF-based assay, both as described in Example 4 above. The results are summarized in Table 6. Overall, with this particular HIV-1 strain (RF) and host cell line (CEM-SS), calanolide A most consistently gave the highest antiviral potency (lowest $EC_{50}$); 7,8-dihydrocalanolide A and costatolide were approximately equipotent and about 2/3 the potency of calanolide A; 7,8-dihydrocostatolide was about 1/3 as potent as calanolide A. The direct cytotoxicity of the compounds to the CEM-SS target cells was greatest (lowest $IC_{50}$) for costatolide; however, it was somewhat less for 7,8-dihydrocostatolide, which in turn was more comparable to calanolide A and 7,8-dihydrocalanolide A. The in vitro "therapeutic index" (TI) was consistently greatest for calanolide A and 7,8-dihydrocalanolide A.

TABLE 6

Comparison of antiviral activities ($EC_{50'\!s}$) and cytotoxicities ($IC_{50'\!s}$) of calanolide A, 7,8-dihydro(DH)calanolide A, costatolide, and 7,8-dihydro(DH)costatolide from quadruplicate tests of each compound with XTT-based and BCECF-based anti-HIV-1 assays

| Compound | $EC_{50}$ μM (±SD) | | $IC_{50}$ μM (±SD) | | TI ($IC_{50}/EC_{50}$) | |
|---|---|---|---|---|---|---|
| | XXT | BCECF | XTT | BCECF | XTT | BCECF |
| Calanolide A | 0.13 (0.01) | 0.16 (0.09) | 14.3 (1.65) | 14.3 (1.83) | 110 | 89 |
| DH-calanolide A | 0.23 (0.03) | 0.19 (0.07) | 12.5 (1.12) | 18.7 (1.95) | 54 | 98 |
| Costatolide | 0.23 (0.04) | 0.20 (0.07) | 10.0 (0.41) | 8.0 (0.97) | 43 | 40 |
| DH-costatolide | 0.30 (0.01) | 0.31 (0.06) | 18.7 (1.33) | 10.3 (3.06) | 62 | 33 |

Quadruplicate tests of each of the above four compounds on HIV-1 reproductive indices (also assayed as described in Example 4 above) yielded the results set forth in Table 7, which are consistent with the results and conclusions from Table 6.

TABLE 7

Comparison of in vitro suppression of supernatant viral reproductive indices (viral core protein [p24]; reverse transcriptase [RT], and syncytium-forming units [SFU]) by calanolide A, 7,8-dihydrocalanolide A, costatolide, and 7,8-dihydrocostatolide

| Compound | $EC_{50}$ μM (±S.D.) | | |
|---|---|---|---|
| | p24 | RT | SFU |
| Calanolide A | 0.07 (0.01) | 0.07 (0.01) | 0.08 (0.02) |
| DH-calanolide A | 0.12 (0.02) | 0.13 (0.03) | 0.17 (0.03) |
| Costatolide | 0.11 (0.03) | 0.12 (0.04) | 0.14 (0.07) |
| DH-costatolide | 0.24 (0.04) | 0.25 (0.30) | 0.19 (0.11) |

All references identified herein (including publications, patents, patent applications, and the like) are hereby incorporated by reference in their entireties.

While this invention has been described with emphasis upon preferred embodiments, it will be obvious to those of ordinary skill in the art that the preferred compounds, compositions, and methods may be varied. It is intended that the invention may be practiced otherwise than as specifically described herein. Accordingly, this invention includes all modifications encompassed within the spirit and scope of the following claims.

What is claimed is:

1. A method of treating a HIV-1 infection, which method comprises administering to a human an anti-HIV-1 effective amount of at least one compound selected from the group consisting of:

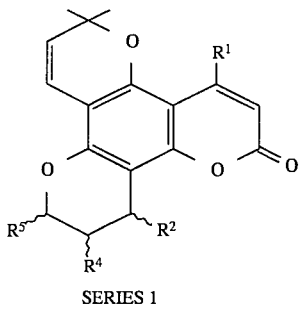

SERIES 1 and

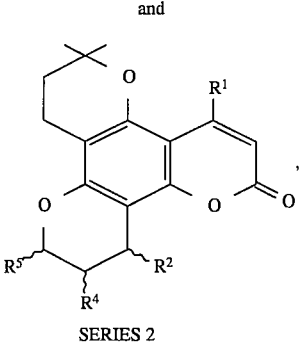

SERIES 2 wherein $R^1$ is $C_1$–$C_6$ alkyl or aryl; $R^2$ is ◀ OH, ⋯ $OR^3$, ⋯ $OR^3$, ◀ $O_2CR^3$, ⋯ $O_2CR^3$, ◀ $O_3SR^3$, or ⋯ OH, ◀ $O_3SR^3$; wherein $R^3$ is $C_1$–$C_6$ alkyl or aryl; and $R^4$ and $R^5$ are the same or different and are each ◀ $CH_3$ or ⋯ $CH_3$.

2. The method of claim 1, which further comprises co-administering an anti-HIV-1 effective amount of at least one additional antiviral compound other than said compound.

3. The method of claim 1, wherein $R^3$ is $C_1$–$C_6$ alkyl or phenyl.

4. The method of claim 3, which further comprises co-administering an anti-HIV-1 effective amount of at least one additional antiviral compound other than said compound.

5. The method of claim 3, wherein said compound is selected from the group consisting of calanolide A, dihydrocalanolide A, calanolide B, and dihydrocalanolide B.

6. The method of claim 5, which further comprises co-administering an anti-HIV-1 effective amount of at least one additional antiviral compound other than said compound.

7. A compound, in substantially pure form, selected from the group consisting of calanolide A, dihydrocalanolide A, calanolide B, dihydrocalanolide B, and dihydrosoulattrolide.

8. The compound of claim 7, in substantially pure form, which is calanolide A.

9. The compound of claim 7, in substantially pure form, which is dihydrocalanolide A.

10. The compound of claim 7, in substantially pure form, which is calanolide B.

11. The compound of claim 7, in substantially pure form, which is dihydrocalanolide B.

12. The compound of claim 7, in substantially pure form, which is dihydrosoulattrolide.

13. A method of isolating an antiretroviral compound of claim 1 from plants of the genus Calophyllum, which method comprises the step of:

(a) extracting plant material with an organic solvent to obtain a crude extract having antiretroviral activity;

(b) solvent-solvent partitioning said crude extract as necessary to concentrate an antiretroviral compound in a nonpolar fraction;

(c) subjecting said crude extract or said nonpolar fraction to gel permeation or vacuum liquid chromatography as necessary to further concentrate said antiretroviral compound; and (d) isolating and purifying said antiretroviral compound by HPLC on silica gel and $C_{18}$ reversed-phase columns.

14. The method of claim 13, wherein said plant material consists of leaves, stems, twigs, fruits, flowers, wood, bark or roots of the said Calophyllum plants.

15. The method of claim 13, wherein said plant material consists of latex from the said Calophyllum plants.

16. The method of claim 15, wherein said latex is obtained non-destructively from Calophyllum plants by the steps of:

(a) making multiple superficial slashes to the trunkbark, extending to but not through the cambium layer; and (b) periodically scraping the accumulated latex from the slashed surfaces.

17. The method of claim 13, wherein said plant material is from *Calophyllum lanigerum* Miq.

18. The method of claim 17, wherein said plant material is from *Calophyllum lanigerum* Miq. var. austrocoriaceum (T. C. Whitmore) P. F. Stevens.

19. The method of claim 13, wherein said plant material is from *Calophyllum teysmannii* Miq.

20. The method of claim 19, wherein said plant material is from *Calophyllum teysmannii* Miq. var. inophylloide (King) P. F. Stevens.

21. The method of claim 20 wherein said plant material is latex and said antiretroviral compound is costatolide or soulattrolide.

22. A pharmaceutical composition which comprises a pharmaceutically acceptable carrier and an anti-HIV-1 effective amount of at least one compound selected from the group consisting of calanolide A, dihydrocalanolide A, calanolide B, dihydrocalanolide B, and dihydrosoulattrolide.

23. The composition of claim 22, wherein said compound is selected from the group consisting of calanolide A, dihydrocalanolide A, calanolide B, and dihydrocalanolide B.

24. The composition of claim 22, which further comprises an anti-HIV-1 effective amount of at least one additional anti-HIV-1 compound other than a compound selected from the group consisting of calanolide A, dihydrocalanolide A, calanolide B, dihydrocalanolide B, costatolide, dihydrocostatolide, soulattrolide, and dihydrosoulattrolide.

* * * * *